(12) United States Patent
Patwardhan et al.

(10) Patent No.: US 8,709,391 B2
(45) Date of Patent: Apr. 29, 2014

(54) FAMILY OF PAIN PRODUCING SUBSTANCES AND METHODS TO PRODUCE NOVEL ANALGESIC DRUGS

(75) Inventors: Amol Madhusudan Patwardhan, Tucson, AZ (US); Kenneth Michael Hargreaves, San Antonio, TX (US); Armen Norakovich Akopian, San Antonio, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 121 days.

(21) Appl. No.: 13/131,220

(22) PCT Filed: Nov. 24, 2009

(86) PCT No.: PCT/US2009/065739
§ 371 (c)(1),
(2), (4) Date: Aug. 15, 2011

(87) PCT Pub. No.: WO2010/062900
PCT Pub. Date: Jun. 3, 2010

(65) Prior Publication Data
US 2011/0311545 A1 Dec. 22, 2011

Related U.S. Application Data

(60) Provisional application No. 61/118,078, filed on Nov. 26, 2008.

(51) Int. Cl.
*A61K 31/74* (2006.01)
(52) U.S. Cl.
USPC ..................... 424/78.02; 424/78.06
(58) Field of Classification Search
None
See application file for complete search history.

(56) References Cited

U.S. PATENT DOCUMENTS

| | | | |
|---|---|---|---|
| 5,773,209 A * | 6/1998 | Medford et al. | 435/7.24 |
| 5,914,129 A | 6/1999 | Mauskop | |
| 6,518,311 B2 | 2/2003 | Kozak et al. | |
| 2005/0261254 A1 | 11/2005 | Lockwood et al. | |
| 2007/0207503 A1 | 9/2007 | Kim et al. | |
| 2007/0275093 A1 * | 11/2007 | Pierard et al. | 424/642 |

FOREIGN PATENT DOCUMENTS

| | | |
|---|---|---|
| EP | 1787679 | 5/2007 |
| WO | 99/56761 | 11/1999 |
| WO | 02/09725 | 2/2002 |
| WO | 02/084287 | 10/2002 |
| WO | WO 2005/041955 A1 * | 5/2005 ........... A61K 31/415 |

OTHER PUBLICATIONS

Ferrando et al. 'Restoration of hormonal action and muscle protein.' Crit. Care Med 35[Suppl.]:S630-S634, 2007.*
Malenfant et al. "Prevalence and characteristics of chronic sensory problems in burn patients" Pain 67 (1996) 493-500.
Laborde "Burn epidemiology: the patient, the nation, the statistics, and the data resources" Crit Care Nurs Clin N Am 16 (2004) 13-25.
Summer et al "Burn Injury Pain: The Continuing Challenge" The Journal of Pain, vol. 8, No. 7 Jul. 2007: pp. 533-548.
McLure et al. "Review of local anaesthetic agents" Minerva Anestesiol 2005;71:59-74.
Brown et al. "Opioid and Benzodiazepine Withdrawal Syndrome in Adult Burn Patients" The American Surgeon, 66 (2000), 367-371.
Coleman "Bupivacaine and Ventricular Fibrillation" Anestii Analc 2004; 99, 1269.
Coderre et al. "Cutaneous hyperalgesia: contributions of the peripheral and central nervous systems to the increase in pain sensitivity after injury" Brain Research, 404 (1987) 95-106.
Raja et al. "Evidence for different mechanisms of primary and secondary hyperalgesia following heat injury to the glabrous skin" Brain (1984), 107, 1179-1188.
Summer et al. "TrkA and PKC-epl!silon in Thermal Burn-Induced Mechanical Hyperalgesia in the Rat" The Journal of Pain, vol. 7, No. 12 Dec. 2006: pp. 884-891.
Summer et al. "Pro inflammatory cytokines mediating burn-injury pain" Pain 135 (2008) 98-107.
Pedersen et al. "Secondary hyperalgesia to heat stimuli after burn injury in man" Pain 76 (1998) 377-384.
Bolcskei et al. "Investigation of the role of TRPVI receptors in acute and chronic nociceptive processes using gene-deficient mice" Pain 117 (2005) 368-376.
Lamotte et al. "Peripheral Neural Mechanisms of Cutaneous Hyperalgesia Following Mild Injury by Heat" The Journal of Neuroscience, vol. 2, No. 6, pp. 765-781, Jun. 1982.
Caterina et al. "The capsaicin receptor: a heat-activated ion channel in the pain pathway" Nature, vol. 389, Oct. 1997, pp. 816-824.
Caterina et al. "Impaired Nociception and Pain Sensation in Mice Lacking the Capsaicin Receptor" Science, vol. 288 (2000), 306-313.

(Continued)

*Primary Examiner* — Nora Rooney
(74) *Attorney, Agent, or Firm* — Meyertons, Hood, Kivlin, Kowert & Goetzel, P.C.; Eric B. Meyertons

(57) ABSTRACT

A method may include treating pain, shock, and/or inflammatory conditions in a subject. A method may include using a therapeutically effective amount of an antibody, a lipoxygenase inhibitor, a cytochrome P-450 enzyme inhibitor, and/or an antioxidant configurable to at least partially treat pain, shock, and/or inflammatory conditions in a subject. A method of treating pain, shock, and/or inflammatory conditions in a subject may include inactivating or preventing at least one linoleic acid metabolite to treat certain conditions (e.g., pain, shock, and/or inflammation).

2 Claims, 19 Drawing Sheets

(56) References Cited

OTHER PUBLICATIONS

Walker et al. "The VR1 Antagonist Capsazepine Reverses Mechanical Hyperalgesia in Models of Inflammatory and Neuropathic Pain" Journal of Pharmacology and Experimental Therapeutics, 304(1), 56-62, (2003).
Barton et al. "Attenuation of experimental arthritis in TRPVIR knockout mice" Experimental and Molecular Pathology, 81, (2006) 166-170.
Carlton et al. "Peripheral capsaicin receptors increase in the inflamed rat hindpaw: a possible mechanism for peripheral sensitization" Neuroscience Letters 310 (2001) 53-56.
Chizh et al. "The effects of the TRPVI antagonist SB-705498 on TRPVI receptor-mediated activity and inflammatory hyperalgesia in humans" Pain 132 (2007) 132-141.
Cortright et al. "Biochemical pharmacology of the vanilloid receptor TRPV1" Eur. J. Biochem. 271, 1814-1819 (2004).
Diogenes et al. "Prolactin Modulates TRPVI in Female Rat Trigeminal Sensory Neurons" The Journal of Neuroscience, (2006), 26(31), 8126-8136.
Van Buren et al. "Sensitization and translocation of TRPV I by insulin and IGF-1" Molecular Pain, 2005, 1:17.
Bhave et al. "cAMP-Dependent Protein Kinase Regulates Desensitization of the Capsaicin Receptor {VR1} by Direct Phosphorylation" Neuron, vol. 35, 721-731, Aug. 15, 2002.
Premkumar et al. "Induction of vanilloid receptor channel activity by protein kinase c" Nature, (2000), 408:21, 985-990.
Bonnington et al. "Signalling pathways involved in the sensitisation of mouse nociceptive neurones by nerve growth factor" J Physiol ( 2003 ), 551.2, 433-446.
Zhang et al. "NGF rapidly increases membrane expression of TRPV1 heat-gated ion channels" The EMBO Journal (2005) 24, 4211-4223.
Gavva et al. "The Vanilloid Receptor TRPVI Is Tonically Activated In Vivo and Involved in Body Temperature Regulation" The Journal of Neuroscience, (2007), 27(13), 3366-3374.
Steiner et al. "Nonthermal Activation of Transient Receptor Potential Vanilloid-1 Channels in Abdominal Viscera Tonically Inhibits Autonomic Cold-Defense Effectors" The Journal of Neuroscience, (2007), 27(28), 7459-7468.
Hwang et al. "Direct activation of capsaicin receptors by products of lipoxygenases: Endogenous capsaicin-like substances" PNAS, (2000), 97(11), 6155-6160.
Ahern et al. "Polyamines Are Potent Ligands for the Capsaicin Receptor TRPV1" Journal of Biological Chemistry, (2006), 281(13), 8991-8995.
Huang et al. "An endogenous capsaicin-like substance with high potency at recombinant and native vanilloid VR1 receptors" PNAS (2002), 99:12, 8400-8405.
Chu et al. "N-Oleoyldopamine, a Novel Endogenous Capsaicin-like Lipid That Produces Hyperalgesia" Journal of Biological Chemistry (2003) 278(16),13633-13639.
Movahed et al. "Endogenous Unsaturated C18 N-Acylethanolamines Are Vanilloid Receptor (TRPV1) Agonists" Journal of Biological Chemistry (2005) 280(46),38496-38504.
Zygmunt et al. "Vanilloid receptors on sensory nerves mediate the vasodilator action of anandamide" Nature (1999), 400:29, 452-457.
Shin et al. "Bradykinin-12-lipoxygenase-VR1 signaling pathway for inflammatory hyperalgesia" PNAS (2002), 99:15, 10150-10155.
Dinis et al. "Anandamide-Evoked Activation of Vanilloid Receptor 1 Contributes to the Development of Bladder Hyperreflexia and Nociceptive Transmission to Spinal Dorsal Horn Neurons in Cystitis" The Journal of Neuroscience (2004), 24:50, 11253-11263.
Brauchi et al. "Dissection of the components for PIP2 activation and thermosensation in TRP channels" PNAS (2007), 104:24, 10246-10251.
Voets et al. "The principle of temperature-dependent gating in cold- and heat-sensitive TRP channels" Nature (2004) 430:12, 748-754.
Tominaga et al. "Thermosensation and Pain" J Neurobiol 61, 3-12 (2004).
Cui et al. "TRPV1 receptors in the CNS play a key role in broad-spectrum analgesia of TRPV1 antagonists" J Neurosci 26, 9385-93 (2006).
Hanaki et al. "Leukotoxin, 9, 10-epoxy-12-octadecenoate: a possible responsible factor in circulatory shock and disseminated intravascular coagulation" Jpn J Med 30, 224-8 (1991).
Kosaka et al. "Leukotoxin, a linoleate epoxide: its implication in the late death of patients with extensive burns" Mol Cell Biochem 139, 141-8 (1994).
Hayakawa et al. "Proposal of leukotoxin, 9,10-epoxy-12-octadecenoate, as a burn toxin" Biochem Int 21, 573-9 (1990).
Yoshida et al. "Bio-markers of lipid peroxidation in vivo: hydroxyoctadecadienoic acid and hydroxycholesterol" Biofactors 27, 195-202 (2006).
Goodman et al. "Nordihydroguaiaretic acid protects hippocampal neurons against amyloid beta-peptide toxicity, and attenuates free radical and calcium accumulation" Brain Res 654, 171-6 (1994).
Dupont et al. "New bis-catechols 5-lipoxygenase inhibitors" Bioorg Med Chem 9, 229-35 (2001).
Spindler et al. "Significance and Immunoassay of 9- and 13-Hydroxyoctadecadienoic Acids" Biochemical and Biophysical Research Communications, 218, 187-191 (1996).
Kim et al. "Effects of nordihydroguaiaretic acid on Na+ currents in rat dorsal root ganglion neurons" Brain Research, 1072 (2006) 62-71.
Arteaga et al. "*Larrea tridentata* (Creosote bush), an abundant plant of Mexican and US-American deserts and its metabolite nordihydroguaiaretic acid" Journal of Ethnopharmacology 98 (2005) 231-239.
Trang et al. "Involvement of spinal lipoxygenase metabolites in hyperalgesia and opioid tolerance" European Journal of Pharmacology 491 (2004) 21-30.
Carey et al "Simple Procedure for Measuring the Pharmacodynamics and Analgesic Potential of Lipoxygenase Inhibitors" Journal of Pharmacological Methods 20, 347-356 (1988).
Bahr et al. "Influence of Inhibitors of the Eicosanoid Metabolism, and of Eicosanoids- and PAF-Acether Antagonists on Mortality and some Biochemical Parameters of Three Shock Models" Prostaglandins in Clinical Research: Cardiovascular System, pp. 229-233 (1989).
Ahern "Activation of TRPV1 by the Satiety Factor Oleoylethanolamide" Journal of Biological Chemistry (2003), 278:33, 30429-30434.
Matta et al. "TRPV1 is a novel target for omega-3 polyunsaturated fatty acids" J Physiol. 578.2 (2007) 397-411.
Munroe "Inhibitory Effects of Ketoconazole on the Oxidation of Linoleic Acid Micelles, Phospholipid Liposomes, and Human Low Density Lipoprotein (H-LDL)" Master's Thesis, Drake University, 1993.
Inceoglu et al. "Inhibition of soluble epoxide hydrolase reduces LPS-induced thermal hyperalgesia and mechanical allodynia in a rat model of inflammatory pain" Life Sci. (2006) 79(24), 2311-2319.

\* cited by examiner

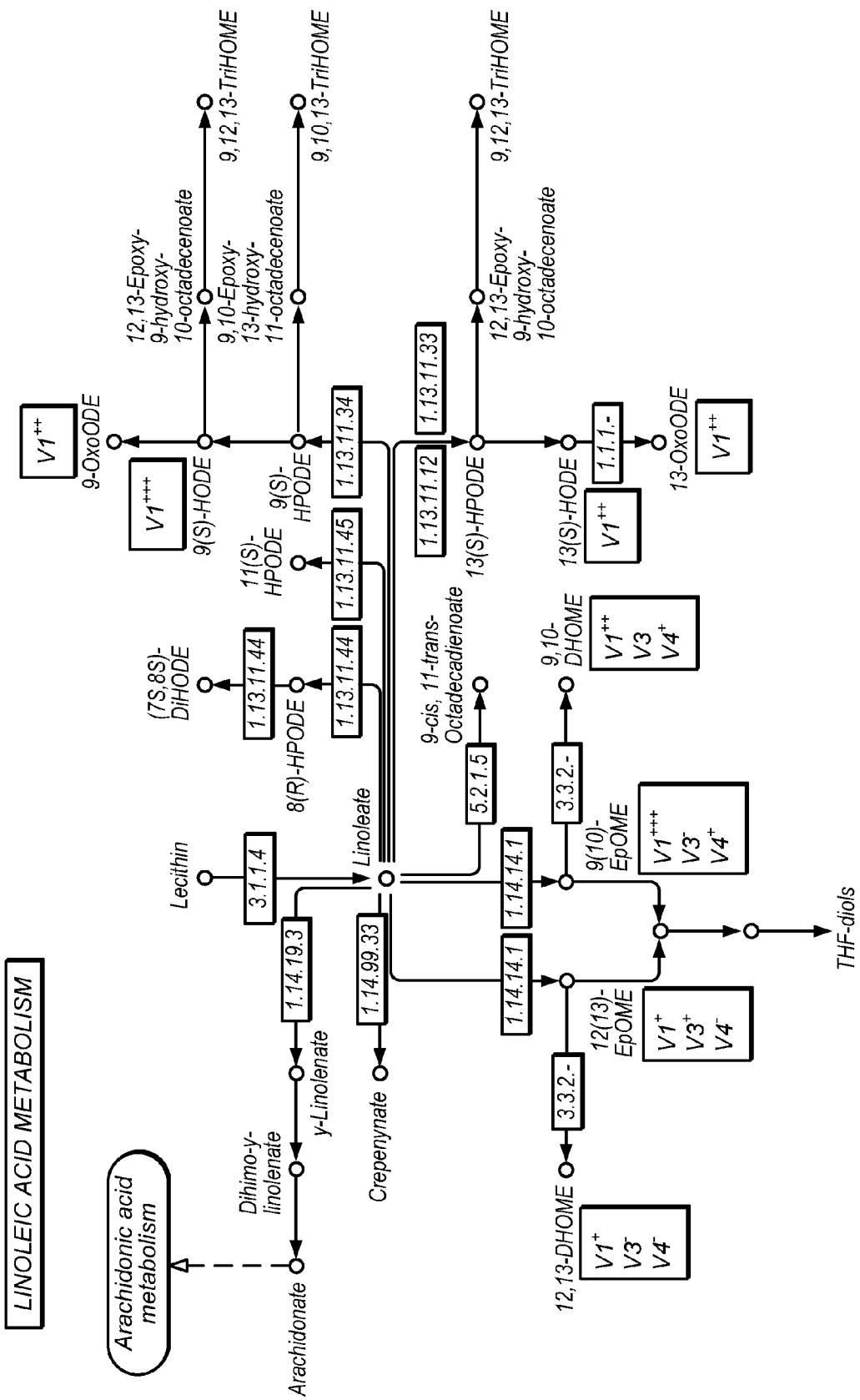
FIG. 7 LINOLEIC ACID METABOLISM

FAMILY OF PAIN PRODUCING SUBSTANCES AND METHODS TO PRODUCE NOVEL ANALGESIC DRUGS

PRIORITY CLAIM

This application is a 371 of PCT Application PCT/US2009/065739, filed Nov. 24, 2009, which claims priority to U.S. Provisional Application Ser. No. 61/118,078, filed Nov. 26, 2008.

STATEMENT ON U.S. FEDERALLY SPONSORED RESEARCH OR DEVELOPMENT

This invention was made with government support under NIH Grant No. R01 DA19585 awarded by the National Institutes of Health. Accordingly, the United States Government may have certain rights in this invention.

BACKGROUND OF THE INVENTION

1. Field of the Invention

The present invention generally relates to the fields of treating a pain, shock, and/or inflammatory condition in a subject. More specifically, the present invention is related to the use of a pharmaceutical composition that comprises one or more compounds that inhibit and/or minimize the production of oxidized linoleic acid metabolites and/or block the activity of oxidized linoleic acid metabolites.

2. Description of the Relevant Art

Many pain conditions are poorly managed by currently available analgesics. For example, burn injuries affect more than two million people annually in the United States alone. Importantly, poor pain control in burn patients is known to increase the risk for long term adverse outcomes. This is a critical issue since surveys indicate that about one-half of burned patients have inadequate pain management. Patients suffering from a burn injury experience pain at the initial heat insult, during healing, and even in a chronic form, post burn injury.

Currently available analgesics for treating burn pain (eg., opiates, local anesthetics) demonstrate only limited efficacy and are associated with considerable adverse effects. In addition to burn pain, there are many other pain states (e.g., inflammatory pain, neuropathic pain, cancer pain, herpes zoster pain, etc) for which currently available analgesics exhibit very limited activity, especially with repeated dosing.

Shock resulting from massive trauma, severe blood or fluid loss, systemic infections, insufficient cardiac output, or any other disorder or injury that leads to a hypoperfusional state is a serious, life threatening condition. Even with aggressive and prompt treatment shock is often fatal.

It is therefore desirable to develop a safer method of treating a pain, shock, and/or inflammatory condition in a subject.

SUMMARY

In some embodiments, one or more compounds that inhibit and/or minimize the production of oxidized linoleic acid metabolites and/or block the activity of oxidized linoleic acid metabolites may be used in the preparation of a pharmaceutical composition for treating pain, shock, inflammatory conditions, or combinations thereof, in a mammal in need thereof.

A pharmaceutical composition for treating pain, shock, inflammatory conditions, or combinations thereof in a subject may include one or more compounds that inhibit and/or minimize the production of oxidized linoleic acid metabolites and/or block the activity of oxidized linoleic acid metabolites and one or more pharmaceutically acceptable carriers.

In some embodiments, the pharmaceutical composition comprises one or more compounds that block the activity of oxidized linoleic acid metabolites, wherein at least one of the compounds is an antibody that binds to at least one oxidized linoleic acid metabolite. Antibodies that may be used in the pharmaceutical composition include antibodies that bind to a hydroxy linoleic acid metabolite, antibodies that bind to an epoxy linoleic acid metabolite, and antibodies that bind to an oxo linoleic acid metabolite. Examples of linoleic acid metabolites that the antibody binds to include, but are not limited to: (10E,12Z)-9-oxooctadeca-10,12-dienoic acid; (9Z,11E)-13-oxooctadeca-9,11-dienoic acid; 9-hydroxyoctadecadienoic acid; 13-hydroxyoctadecadienoic acid; 9(10)-dihydroxy-octadec-12-enoic acid; 12,13-dihydroxy-9Z-octadecenoic acid; (12Z)-9,10-epoxyoctadecenoic acid; 12,13-epoxyoctadec-9Z-enoic acid. The antibody may be a monoclonal antibody or a polyclonal antibody.

In an embodiment, the pharmaceutical composition may include one or more compounds that inhibit and/or minimize the production of oxidized linoleic acid metabolites. In one embodiment, wherein at least one of the compounds that inhibit and/or minimize the production of oxidized linoleic acid metabolites is a cytochrome P-450 enzyme inhibitor.

In an embodiment, the pharmaceutical composition may include one or more compounds that inhibit and/or minimize the production of oxidized linoleic acid metabolites. In one embodiment, at least one of the compounds is an antioxidant sufficient to substantially inhibit and/or reduce the catalytic effect of relevant metabolic enzymes in the Linoleate pathway.

In an embodiment, a method of treating pain, shock, inflammatory conditions, or combinations thereof in a subject includes administering to a subject who would benefit from such treatment a therapeutically effective amount of a pharmaceutical composition, wherein the pharmaceutical composition comprises one or more compounds that inhibit and/or minimize the production of oxidized linoleic acid metabolites and/or block the activity of oxidized linoleic acid metabolites. The pharmaceutical composition may be administered intravenously, orally, topically, or directly into the central nervous system.

BRIEF DESCRIPTION OF THE DRAWINGS

Advantages of the present invention may become apparent to those skilled in the art with the benefit of the following detailed description of the preferred embodiments and upon reference to the accompanying drawings described herein below.

FIG. 7 depicts a summary of activity of Linoleic acid metabolites on various TRP channels. The pathway is obtained from the website: http://www.genome.ad.jp/kegg/pathway/map/map00591.html

Figure 1A:
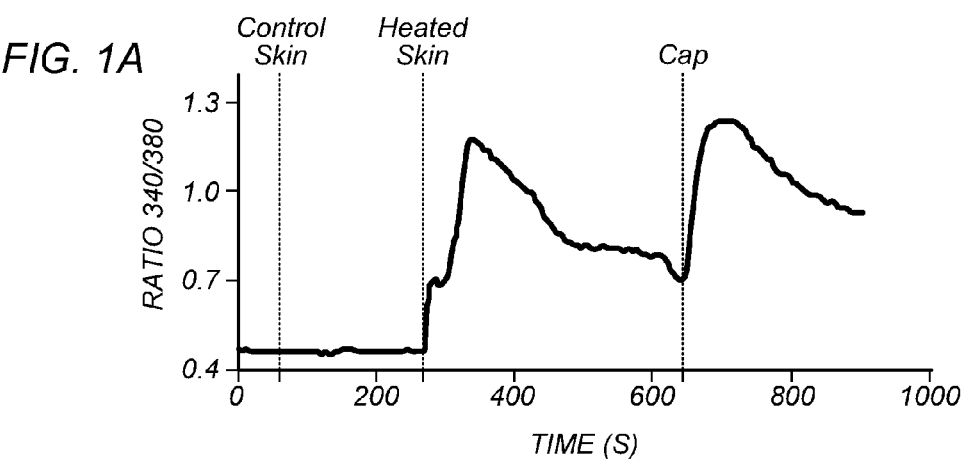
FIG. 1A depicts a graphical evaluation of the release of a TRPV1 agonist from superfusates of control and heated skin.
Figure 1B:
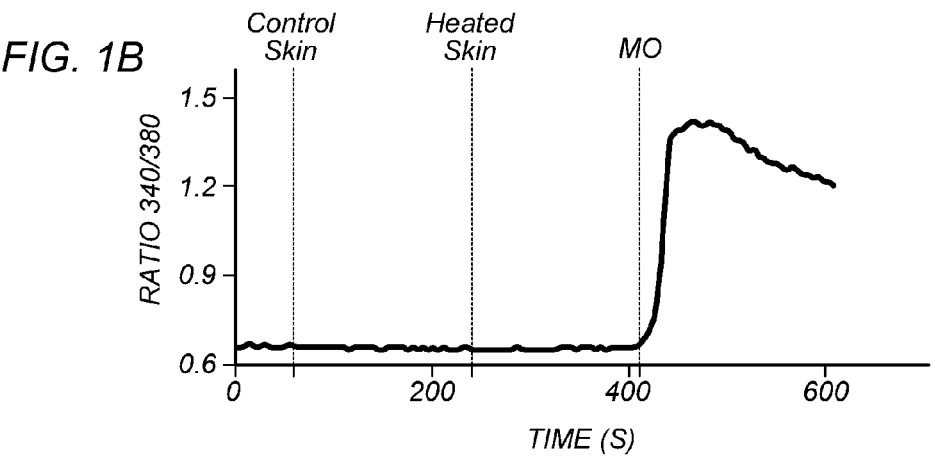
FIG. 1B depicts a graphical evaluation of the excitatory effect of superfusates collected from heated skin when applied to TG neurons from TRPV1 KO mice.
Figure 1C:
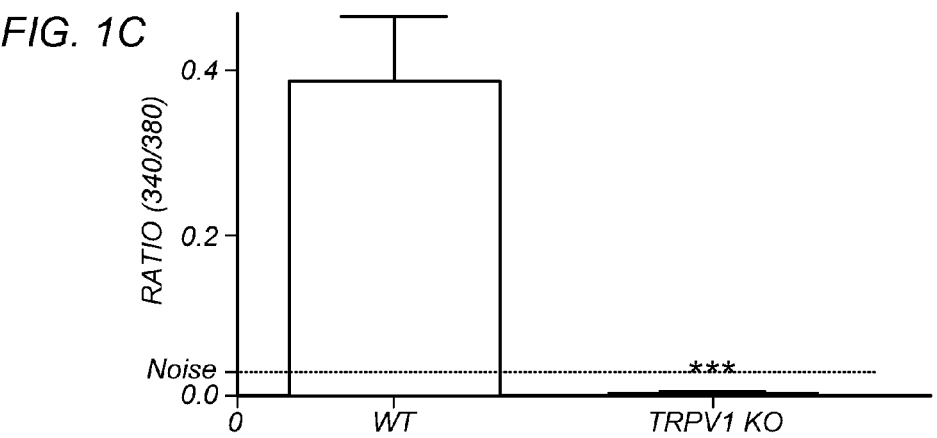
FIG. 1C depicts a bar graph summarizing the experimental results from the experiments of FIGS. 1A and 1B.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DEFINITIONS

The terms used throughout this specification generally have their ordinary meanings in the art, within the context of the invention, and in the specific context where each term is used. Certain terms are discussed below, or elsewhere in the specification, to provide additional guidance to the practitioner in describing the devices and methods of the invention and how to make and use them. It will be appreciated that the same thing can be said in more than one way. Consequently, alternative language and synonyms may be used for any one or more of the terms discussed herein, nor is any special significance to be placed upon whether or not a term is elaborated or discussed in greater detail herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term.

As used herein the terms "administration," "administering," or the like, when used in the context of providing a pharmaceutical or nutraceutical composition to a subject generally refers to providing to the subject one or more pharmaceutical, "over-the-counter" (OTC) or nutraceutical compositions in combination with an appropriate delivery vehicle by any means such that the administered compound achieves one or more of the intended biological effects for which the compound was administered. By way of non-limiting example, a composition may be administered by parenteral, subcutaneous, intravenous, intracoronary, rectal, intramuscular, intraperitoneal, transdermal, or buccal routes of delivery. Alternatively, or concurrently, administration may be by the oral route. The dosage administered will be dependent upon the age, health, weight, and/or disease state of the recipient, kind of concurrent treatment, if any, frequency of treatment, and/or the nature of the effect desired. The dosage of pharmacologically active compound that is administered will be dependent upon multiple factors, such as the age, health, weight, and/or disease state of the recipient, concurrent treatments, if any, the frequency of treatment, and/or the nature and magnitude of the biological effect that is desired.

As used herein, the term "agonist" generally refers to a type of ligand or drug that binds and alters the activity of a receptor.

As used herein, the term "antagonist" generally refers to a type of receptor ligand which binds a receptor but which does not alter the activity of the receptor; however when used with an agonist, prevents the binding of the agonist to the receptor hence the effect of the agonist.

As used herein, the term "allodynia" generally refers to pain from stimuli which are not normally painful. The pain may occur other than in the area stimulated. Allodynia may generally refer to other pain.

As used herein, the term "antinociception" generally refers to a reduction in pain sensitivity.

As used herein, the term "monoclonal antibody" generally refers to an antibody obtained from a population of substantially homogeneous antibodies (the individual antibodies comprising the population are identical except for possible naturally occurring mutations that may be present in minor amounts). As used herein, the term "polyclonal antibody" generally refers to a population of antibodies that are directed against a common epitope but which are not identical in structure.

As used herein, terms such as "pharmaceutical composition," "pharmaceutical formulation," "pharmaceutical preparation," or the like, generally refer to formulations that are adapted to deliver a prescribed dosage of one or more pharmacologically active compounds to a cell, a group of cells, an organ or tissue, an animal or a human. Methods of incorporating pharmacologically active compounds into pharmaceutical preparations are widely known in the art. The determination of an appropriate prescribed dosage of a pharmacologically active compound to include in a pharmaceutical composition in order to achieve a desired biological outcome is within the skill level of an ordinary practitioner of the art. A pharmaceutical composition may be provided as sustained-release or timed-release formulations. Such formulations may release a bolus of a compound from the formulation at a desired time, or may ensure a relatively constant amount of the compound present in the dosage is released over a given period of time. Terms such as "sustained release" or "timed release" and the like are widely used in the pharmaceutical arts and are readily understood by a practitioner of ordinary skill in the art. Pharmaceutical preparations may be prepared as solids, semi-solids, gels, hydrogels, liquids, solutions, suspensions, emulsions, aerosols, powders, or combinations thereof. Included in a pharmaceutical preparation may be one or more carriers, preservatives, flavorings, excipients, coatings, stabilizers, binders, solvents and/or auxiliaries that are, typically, pharmacologically inert. It will be readily appreciated by an ordinary practitioner of the art that, pharmaceutical compositions, formulations and preparations may include pharmaceutically acceptable salts of compounds. It will further be appreciated by an ordinary practitioner of the art that the term also encompasses those pharmaceutical compositions that contain an admixture of two or more pharmacologically active compounds, such compounds being administered, for example, as a combination therapy.

As used herein the term "pharmaceutically acceptable salts" includes salts prepared from by reacting pharmaceutically acceptable non-toxic bases or acids, including inorganic or organic bases, with inorganic or organic acids. Pharmaceutically acceptable salts may include salts derived from inorganic bases include aluminum, ammonium, calcium, copper, ferric, ferrous, lithium, magnesium, manganic salts, manganous, potassium, sodium, zinc, etc. Examples include the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-dibenzylethylenediamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, etc.

The terms "reducing," "inhibiting" and "ameliorating," as used herein, when used in the context of modulating a pathological or disease state, generally refers to the prevention and/or reduction of at least a portion of the negative consequences of the disease state. When used in the context of an adverse side effect associated with the administration of a drug to a subject, the term(s) generally refer to a net reduction in the severity or seriousness of said adverse side effects.

As used herein the term "subject" generally refers to a mammal, and in particular to a human.

As used herein, the term "treat" generally refers to an action taken by a caregiver that involves substantially inhibiting, slowing or reversing the progression of a disease, disorder or condition, substantially ameliorating clinical symptoms of a disease disorder or condition, or substantially preventing the appearance of clinical symptoms of a disease, disorder or condition.

Terms such as "in need of treatment," "in need thereof," "benefit from such treatment," and the like, when used in the context of a subject being administered a pharmacologically active composition, generally refers to a judgment made by an appropriate healthcare provider that an individual or animal requires or will benefit from a specified treatment or medical intervention. Such judgments may be made based on a variety of factors that are in the realm of expertise of healthcare providers, but include knowledge that the individual or animal is ill, will be ill, or is at risk of becoming ill, as the result of a condition that may be ameliorated or treated with the specified medical intervention.

By "therapeutically effective amount" is meant an amount of a drug or pharmaceutical composition that will elicit at least one desired biological or physiological response of a cell, a tissue, a system, animal or human that is being sought by a researcher, veterinarian, physician or other caregiver.

Methods and Compositions

Mechanistically, burn injury is a unique type of tissue damage where transient exposure to heat results in long lasting changes in the exposed tissue (e.g., skin). The studies performed in humans and in animals demonstrated that these changes in the damaged tissue are at least in part responsible for the development and maintenance of ongoing pain or hyperalgesia. The heat injured tissue generates various inflammatory mediators that sensitize ion channels such as transient receptor potential vanilloid 1 or TRPV1 to evoke ongoing pain and hyperalgesia. Other important pain conditions include inflammatory, neuropathic, cancer and the like.

TRPV1, also known as the capsaicin receptor, plays a pivotal role in burn injury and other important pain conditions by evoked hyperalgesia and allodynia such that the mice deficient in TRPV1 protein show little to no hyperalgesia in these models. The key role played by TRPV1 in the development of thermal hyperalgesia and possibly mechanical hyperalgesia in various pain models is well established in animal and human studies. Signaling cascades initiated by a variety of inflammatory mediators may sensitize TRPV1 and contribute to inflammatory hyperalgesia. Given the importance of TRPV1 in inflammatory pain, burn pain and cancer pain, including other various pain states, antagonists against TRPV1 may be used for treating pain and/or inflammatory conditions. However, recent studies have demonstrated some serious on target side effects of TRPV1 antagonists that may exclude their clinical use. These data necessitate additional research in findings ways to block TRPV1 activation without using the antagonists.

A variety of endogenous molecules have been shown to activate TRPV1 and they include anandamide, N-arachidonoyl-dopamine, N-oleoyldopamine, polyamines etc. Such endogenous TRPV1 ligands may be generated during inflammation and contribute to constitutive activation of TRPV1. Barring a few reports, the role of these endogenous TRPV1 ligands in physiological or pathological pain is not known. Interestingly, TRPV1 may be activated by stimuli such as protons and noxious heat. The mechanism by which heat activates TRPV1 is not completely understood although several hypotheses have been proposed. Heat may generate endogenous TRPV1-stimulating ligands in the heat-exposed tissue and thus initiates noxious pain sensation. In tissues exposed to heat for longer durations, the endogenous TRPV1 ligands may be constitutively synthesized and activate TRPV1 to produce ongoing pain sensation in the absence of heat. A similar pathway may exist for inflammatory or other pain conditions as well.

In some embodiments, heat injury to organs such as skin results in generation of oxidized linoleic acid metabolites. These metabolites represent a novel family of endogenous TRPV1 ligands. These ligands activate TRPV1 expressed by sensory nerve terminals in the damaged tissue. The opening of TRPV1 leads to generation of action potentials and the pain sensation in the somatosensory cortex.

In some embodiments, metabolites of linoleic acid have been identified as TRPV1 agonists. Linoleic acid is also known by its IUPAC name cis, cis-9,12-octadecadienoic acid. Linoleic acid has a structure:

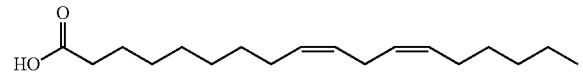

In some embodiments, pharmacological interventions that can block the generation of the endogenous TRPV1 ligand in response to heat may be of therapeutic use. FIG. 7 depicts a summary of activity of Linoleic acid metabolites on various TRP channels and ways of interrupting activity of the metabolites on these channels. In addition, the measurement of Linoleic acid metabolites may constitute a novel method for diagnosing pain or shock conditions, thereby guiding treatment selection.

In some embodiments, oxidized linoleic acid metabolites are generated upon heat stimulation of skin. Oxidized linoleic acid metabolites include, but are not limited to, oxo linoleic acid metabolites, hydroxyl linoleic acid metabolites, and epoxy linoleic acid metabolites. Examples of oxo linoleic acid metabolites include, but are not limited to (10E,12Z)-9-oxooctadeca-10,12-dienoic acid (9-oxoODE, 9-KODE) and (9Z,11E)-13-oxooctadeca-9,11-dienoic acid (13-oxoODE, 13-KODE). Examples of hydroxyl linoleic acid metabolite include, but are not limited to: 9-hydroxyoctadecadienoic acid (9-HODE); 13-hydroxyoctadecadienoic acid (13-HODE); 9(10)-dihydroxy-octadec-12-enoic acid (9,10-DiHOME); and 12,13-dihydroxy-9Z-octadecenoic acid (12,13-DiHOME). Examples of epoxy linoleic acid metabolites include, but are not limited to: (12Z)-9,10-epoxyoctadecenoic acid (9(10)-EpOME) and 12,13-epoxyoctadec-9Z-enoic acid (12(13)-EpOME). It is believed that oxidized linoleic acid metabolites may function as endogenous TRPV1 agonists.

In some embodiments, the blockade of synthesis or immunoneutralization of oxidized linoleic acid metabolites results in decreased activation of pain sensing neurons by heat in vitro and results in thermal antinociception in vivo. Immunoneutralization of oxidized linoleic acid metabolites may be accomplished by the use of one or more antibodies that bind to at least one oxidized linoleic acid metabolite. Antibodies for oxidized linoleic acids may be formed using the procedure of Spindler et al. (Spindler et al. "Significance and immunoassay of 9- and 13-hydroxyoctadecadienoic acids." *Biochem Biophys Res Commun.* 1996; 218:187-191), which is incorporated herein by reference.

TRPV1 is not the only heat-sensitive channel in the body. In some embodiments, other members of the family, TRPV3 and TRPV4 are activated by warm temperatures. Therefore, the linoleic acid metabolites were screened against these channels. In some embodiments, 12,13-EpOME and 9,10-DiHOME are TRPV3 and TRPV4 agonists respectively.

Figure 6:
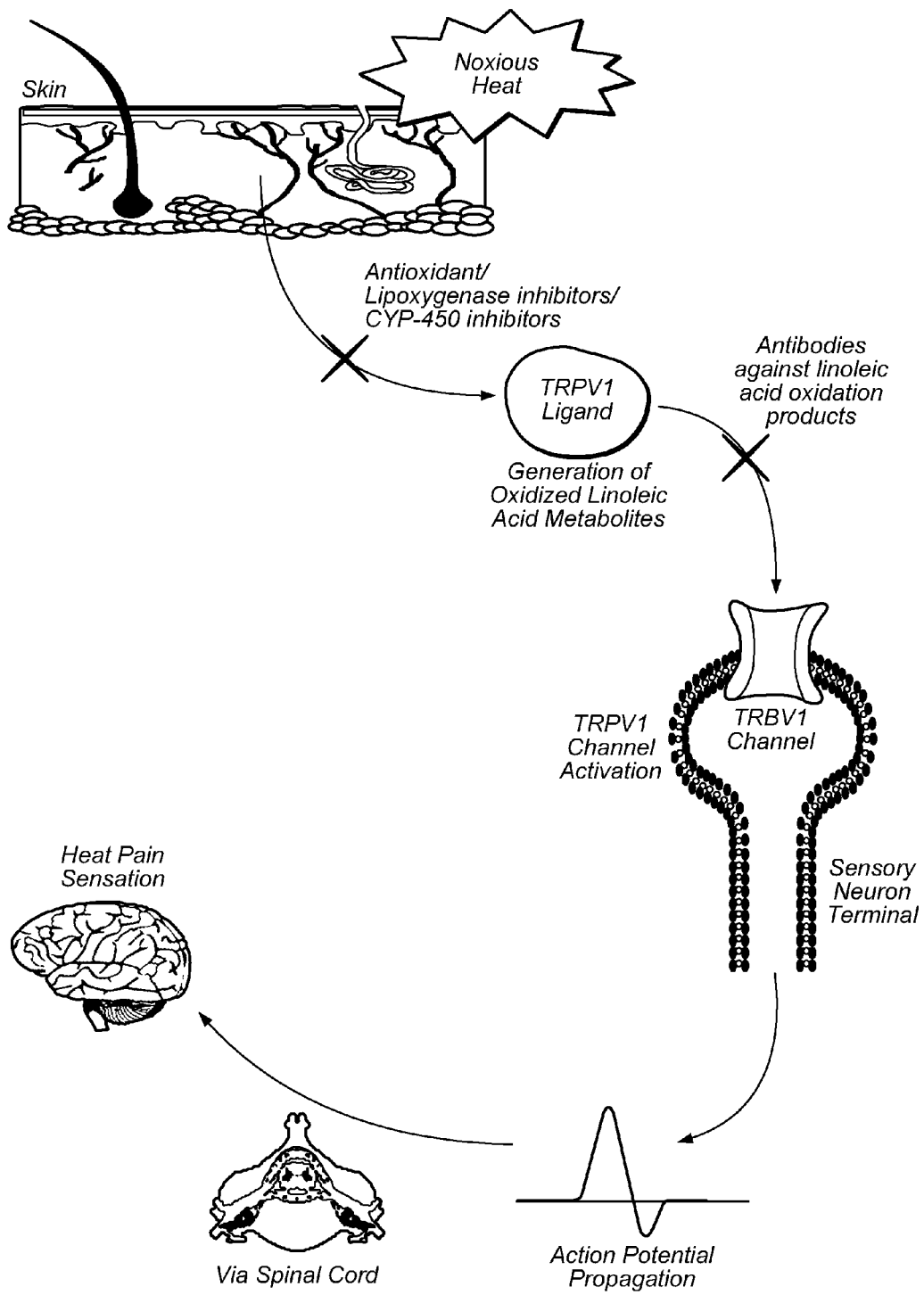
FIG. 6 depicts an schematic diagram of heat injury-evoked nociception and different intervention techniques.

FIG. 6 depicts an embodiment of a model of heat injury-evoked nociception and different intervention embodiments.

In some embodiments, intrathecal application of nordihydroguaiaretic acid (NDGA) or neutralizing antibodies against 9-HODE and 13-HODE may be an effective way to block inflammatory allodynia. Thus compounds such as NDGA and neutralizing antibodies may have two unique sites of action in the treatment of thermal and mechanical allodynia. NDGA is a lipoxygenase (LOX) inhibitor and an antioxidant. LOX inhibitors may be administered sufficiently to substantially attenuate the catalytic effect of enzymes such as EC 1.13.11.34 (aka: arachidonate 5-lipoxygenase) in order to treat pain, shock, and/or inflammatory conditions. In some embodiments, LOX inhibitors other than NDGA may be administered.

In some embodiments, a method of treating a pain, shock and/or inflammatory conditions may include administering a cytochrome P-450 (CYP) enzyme inhibitor sufficient to substantially inhibit and/or reduce the catalytic effect of multiple P450 isozymes capable of synthesizing oxidized linoleic acid metabolites (OLAMs). In some embodiments, the CYP inhibitor may be administered intravenously, orally, topically (for burns or wounds), directly into the central nervous system (e.g., epidural), or any other method described herein or that will be known to those skilled in the art.

In some embodiments, a method of treating a pain, shock and/or inflammatory conditions may include administering a cytochrome P-450 (CYP) isoenzyme inhibitor sufficient to substantially inhibit or reduce the catalytic effect of enzyme EC 1.14.14.1 (aka: CYP2C9 and CYP2C19).

Examples of CYP inhibitors include, but are not limited to; ketoconazole, micronazole, fluconazole, benzbromarone, sulfaphenazole, valproic acid, amiodarone, cimetidine, fenofibrate, fluvastatin, lovastatin, fluvoxamine, sertraline, isoniazid, probenecid, sulfamethoxazole, teniposide, voriconazole, and zafirlukast. In some embodiments, the CYP inhibitor may be administered intravenously, orally, topically (for burns or wounds), directly into the central nervous system (e.g., epidural), or any other method described herein or that will be known to those skilled in the art.

In one embodiment, cytochrome P450 inhibitors that block the formation of linoleic acid metabolites may be used as analgesic drugs. In one embodiment, ketoconazole is administered topically or systemically to relieve pain or inflammation, shock or hypotension mediated by the formation of linoleic acid metabolites.

In some embodiments, a method of treating a pain, shock, and/or inflammatory condition may include administering an antioxidant sufficient to substantially inhibit and/or reduce the catalytic effect of relevant metabolic enzymes in the Linoleate pathway. In some embodiments, antioxidant inhibitors of relevant metabolic enzymes in the Linoleate pathway may include Nordihydroguaiaretic acid (NDGA), Vitamin E and/or Vitamin E derivatives (e.g., water soluble Vitamin E derivative). NDGA may function at least in part as a therapeutic agent due to its strong antioxidant characteristics.

Recent research has indicated that activation of TRPV1 by 9-HODE may have other roles in the body depending upon the expression of TRPV1. TRPV1 in the spinal cord may play an important role in maintenance of thermal and mechanical allodynia in inflammatory or other pain conditions. Depolarization of the spinal cord may lead to the release of 9-HODE and activation of TRPV1. 9-HODE in the spinal cord may lead to development of mechanical allodynia. Similar to heated skin, depolarized spinal cord (with high potassium) may release compound(s) that have TRPV1 agonist activity. Depolarized spinal cord superfusate may contain significantly higher amounts of 9-HODE. Moreover, activation of TRPV1 in the spinal cord by capsaicin (positive control) or by 9-HODE results in tactile allodynia that is completely reversible by a TRPV1 antagonist. Thus, in some embodiments, the role of 9-HODE and similar linoleic acid oxidation products extends beyond heat-nociception.

In some embodiments, a method may include treating shock and/or inflammation. The therapy used to treat any one case of shock depends upon the cause of the patient's hypoperfusional disorder, however, a disruption in cellular membrane integrity, leading to the release and oxidation of linoleic acid metabolites from stressed cells, is a process common to many if not most cases of shock. These oxidized linoleic acid metabolites have paracrine and/or endocrine effects that act to worsen the symptoms of shock. A method as described herein may effectively delay the multi-organ failure associated with Refractory (Irreversible) shock. This therapeutic method may be used in many, if not most cases of shock and save many lives.

In some embodiments, given the role of these metabolites in various other diseases (e.g., arthritis, pulmonary edema and shock), similar methods and antibodies may be used in treating these conditions.

Any suitable route of administration may be employed for providing a subject with an effective dosage of the compositions (e.g., antibodies, compounds) described herein. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The compositions may include those compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, compositions may be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

The pharmaceutical preparations may be manufactured in a manner which is itself known to one skilled in the art, for example, by means of conventional mixing, granulating, dragee-making, softgel encapsulation, dissolving, extracting, or lyophilizing processes. Thus, pharmaceutical preparations for oral use may be obtained by combining the compositions with solid and semi-solid excipients and suitable preservatives, and/or co-antioxidants. Optionally, the resulting mixture may be ground and processed. The resulting mixture of granules may be used, after adding suitable auxiliaries, if desired or necessary, to obtain tablets, softgels, lozenges, capsules, or dragee cores.

Suitable excipients may be fillers such as saccharides (e.g., lactose, sucrose, or mannose), sugar alcohols (e.g., mannitol or sorbitol), cellulose preparations and/or calcium phosphates (e.g., tricalcium phosphate or calcium hydrogen phosphate). In addition binders may be used such as starch paste (e.g., maize or corn starch, wheat starch, rice starch, potato starch, gelatin, tragacanth, methyl cellulose, hydroxypropyl-methylcellulose, sodium carboxymethylcellulose, and/or polyvinyl pyrrolidone). Disintegrating agents may be added (e.g., the above-mentioned starches) as well as carboxymethyl-starch, cross-linked polyvinyl pyrrolidone, agar, or alginic acid or a salt thereof (e.g., sodium alginate). Auxiliaries are, above all, flow-regulating agents and lubricants (e.g., silica, talc, stearic acid or salts thereof, such as magnesium stearate or calcium stearate, and/or polyethylene glycol, or PEG). Dragee cores are provided with suitable coatings, which, if desired, are resistant to gastric juices. Soft gelatin capsules ("softgels") are provided with suitable coatings, which, typically, contain gelatin and/or suitable edible dye(s). Animal component-free and kosher gelatin capsules may be particularly suitable for the embodiments described herein for wide availability of usage and consumption. For this purpose, concentrated saccharide solutions may be used, which may optionally contain gum arabic, talc, polyvinyl pyrrolidone, polyethylene glycol (PEG) and/or titanium dioxide, lacquer solutions and suitable organic solvents or solvent mixtures, including dimethylsulfoxide (DMSO), tetrahydrofuran (THF), acetone, ethanol, or other suitable solvents and co-solvents. In order to produce coatings resistant to gastric juices, solutions of suitable cellulose preparations such as acetylcellulose phthalate or hydroxypropylmethyl-cellulose phthalate, may be used. Dye stuffs or pigments may be added to the tablets or dragee coatings or soft gelatin capsules, for example, for identification or in order to characterize combinations of active compound doses, or to disguise the capsule contents for usage in clinical or other studies.

In some embodiments, compositions (e.g., antibodies) will typically be formulated in such vehicles at a concentration of about 0.1 mg/ml to 100 mg/ml.

For the prevention or treatment of disease, the appropriate dosage of the composition will depend on the type of disease to be treated, as defined above, the severity and course of the disease, whether the compositions are administered for preventive or therapeutic purposes, previous therapy, the patient's clinical history and response to the composition, and the discretion of the attending physician. The composition is suitably administered to the patient at one time or over a series of treatments.

Depending on the type and severity of the disease, about 0.015 to 15 mg/kg of composition (e.g., antibodies) is an initial candidate dosage for administration to the patient, whether, for example, by one or more separate administrations, or by continuous infusion. For repeated administrations over several days or longer, depending on the condition, the treatment is repeated until a desired suppression of disease symptoms occurs. However, other dosage regimens may be useful.

According to another embodiment of the invention, the effectiveness of the composition in preventing or treating disease may be improved by administering the composition serially or in combination with another agent that is effective for those purposes, such as another antibody directed against a different epitope or neutralizing a different protein than the first composition, or one or more conventional therapeutic agents such as, for example, alkylating agents, folic acid antagonists, anti-metabolites of nucleic acid metabolism, antibiotics, pyrimidine analogs, 5-fluorouracil, purine nucleosides, amines, amino acids, triazol nucleosides, corticosteroids, calcium, retinoids, lipoxygenase and cyclooxygenase inhibitors, fumaric acid and its salts, analgesics, psychopharmaceuticals, local anesthetics, spasmolytics, and beta-blockers. Such other agents may be present in the composition being administered or may be administered separately. The composition may be suitably administered serially or in combination with radiological treatments, whether involving irradiation or administration of radioactive substances.

EXAMPLES

Figure 1D:
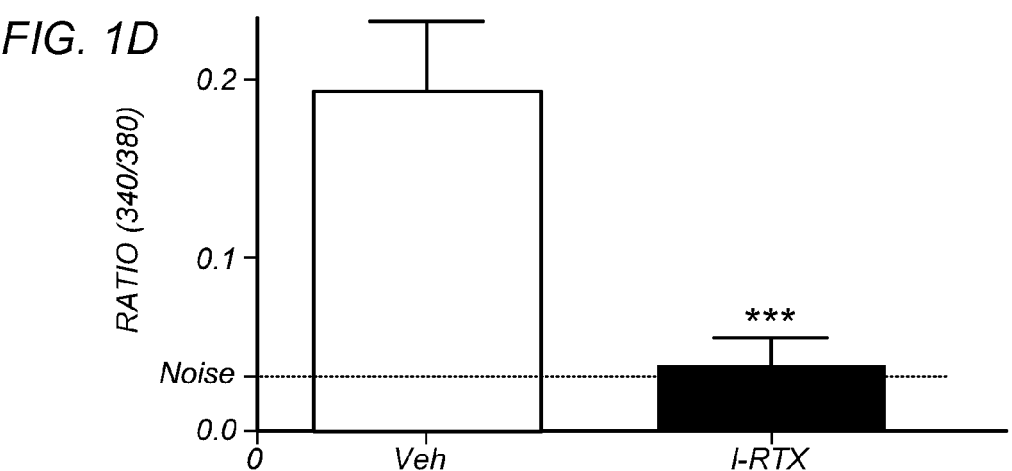
FIG. 1D depicts a bar graph of the results of pretreatment with the TRPV1 antagonist, iodo-resiniferatoxin (I-RTX, 200 nM), versus vehicle on $[Ca^{2+}]i$ levels after application of room temperature superfusates collected from skin biopsies exposed to 48° C.
Figure 1E:
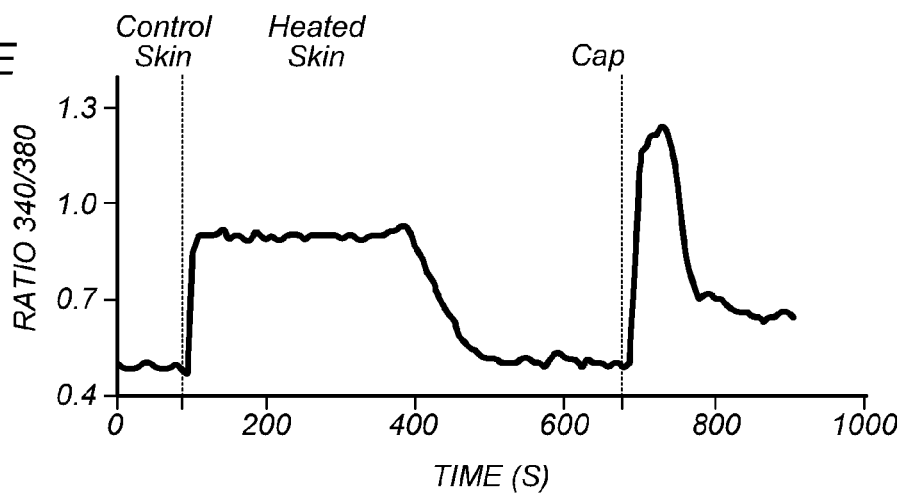
FIG. 1E depicts a time response curve of $[Ca^{2+}]i$ levels demonstrating that heated skin evokes the release of compound(s) that activate CHO cells expressing TRPV1.
Figure 1F:
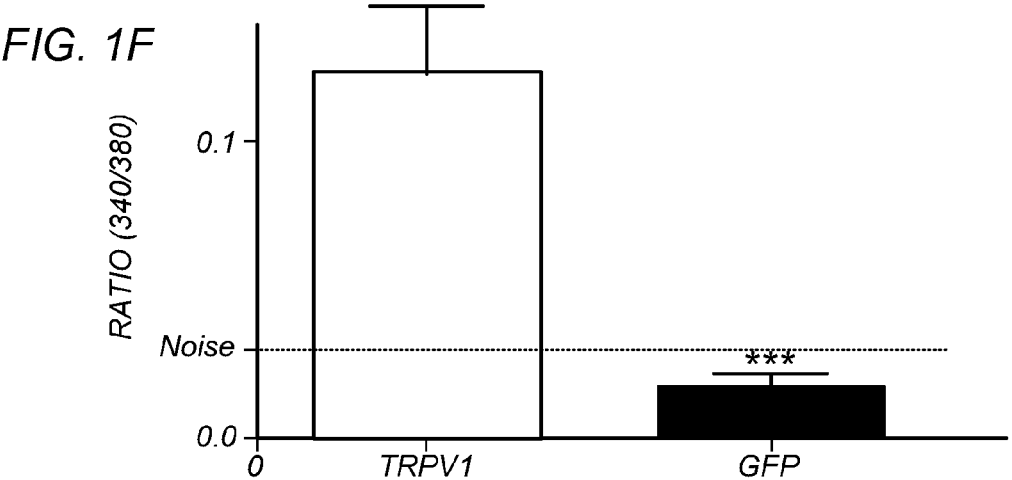
FIG. 1F depicts a bar graph of calcium accumulation evoked by compound(s) released from heated skin in CHOs transfected with either TRPV1 or GFP constructs.
Figure 1G:
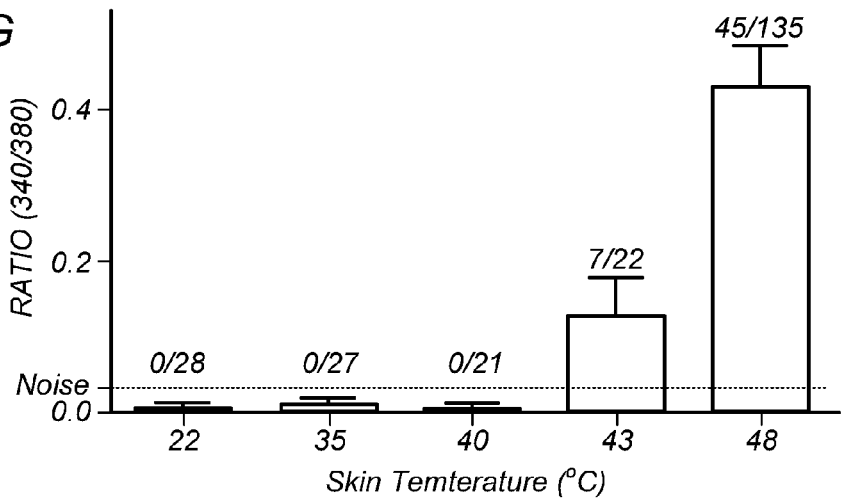
FIG. 1G depicts a comparison of calcium accumulation in cultured rat TG neurons evoked by various supernatants obtained from groups of skin biopsies heated at various temperatures.

FIGS. 1A-H depict that endogenous TRPV1 ligands are generated upon heat insult of mouse skin. The hypothesis of heat-evoked generation of endogenous TRPV1 ligand(s) was evaluated by harvesting mouse skin and then collecting superfusate samples after 20 min exposure to basal (37° C.="control" skin) or noxious (48° C.="heated" skin) temperatures. Aliquots of the two superfusates were applied, at room temperature, to cultured trigeminal ganglia (TG) neurons from wild type (WT) or TRPV1 knock out (TRPV1 KO) mice for measurement of evoked increases in intracellular calcium levels $[Ca^{2+}]i$. In contrast to the supernatants collected from skin exposed to basal temperatures, the application of supernatants collected from heated skin demonstrated a rapid increase in $[Ca^{2+}]i$, but only in those WT neurons that were also capsaicin-sensitive (FIG. 1A). Conversely, there were no changes in $[Ca^{2+}]i$ after application of supernatants from heated skin to either TRPV1 KO cultures (FIG. 1B; mustard oil served as a positive control) or to WT neurons insensitive to capsaicin (data not shown). These data are summarized in FIG. 1C, which indicates that heated skin selectively releases compound(s) that activate TRPV1. Interestingly, superfusate from skins exposed to non-noxious temperature did not contain any substance(s) that activated TG neurons (FIG. 1G). An independent series of control experiments demonstrated that supernatants obtained from heated plastic culture wells (i.e., no skin biopsies) did not alter $[Ca^{2+}]i$ in TG neurons, demonstrating that these liberated compounds were of biological origin (data not shown). Initial characterization studies demonstrated that these compound (s) were unstable at room temperature (>4 h), but could be isolated from $C_{18}$ reverse phase columns using a step gradient of 0-90% acetonitrile; this dried down fraction ($N_2$ gas) was stable at −80° C. for prolonged periods and formed the pool of endogenous compound(s) used in subsequent studies.

Figure 1H:
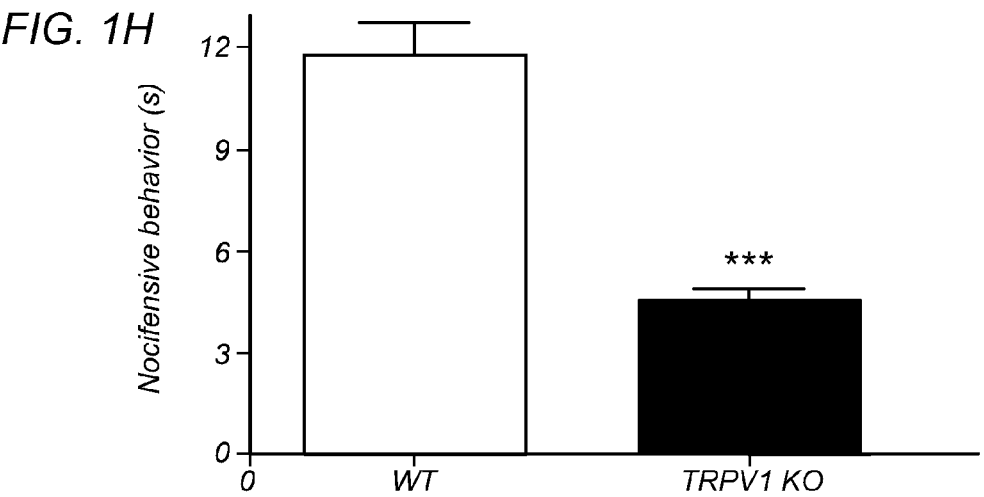
FIG. 1H depicts the effect of ipl injection of compound(s) isolated from heated skin on spontaneous nocifensive behavior in WT vs TRPV1 KO mice.

To further characterize the TRPV1 specificity of these endogenous heat-generated compound(s), the effect of pre-treatment with the TRPV1 antagonist iodo-resiniferatoxin (I-RTX) on the activation of rat TG neurons was evaluated. I-RTX completely blocked the activation of neurons by compound(s) released from heated skin (FIG. 1D). Moreover, application of these compound(s) triggered prompt increases in [Ca]i in CHO cells expressing TRPV1, but not in negative control CHO cells that expressed a GFP construct (FIGS. 1E-F). Next, initial superfusion experiments in isolated mouse skin were expanded by collecting supernatant after exposure to various temperatures and evaluating the release of endogenous TRPV1 compound(s). Such activity was observed in supernatants collected only from skin biopsies exposed to noxious temperatures (43° C. and 48° C.) and not in skin samples exposed to non-noxious temperatures (22-37° C.) (FIG. 1G). Finally, the $C_{18}$ isolated compounds produced significantly greater nocifensive behavior when injected ipl into the hindpaws of WT mice compared with TRPV1 KO mice (FIG. 1H).

Figure 2:
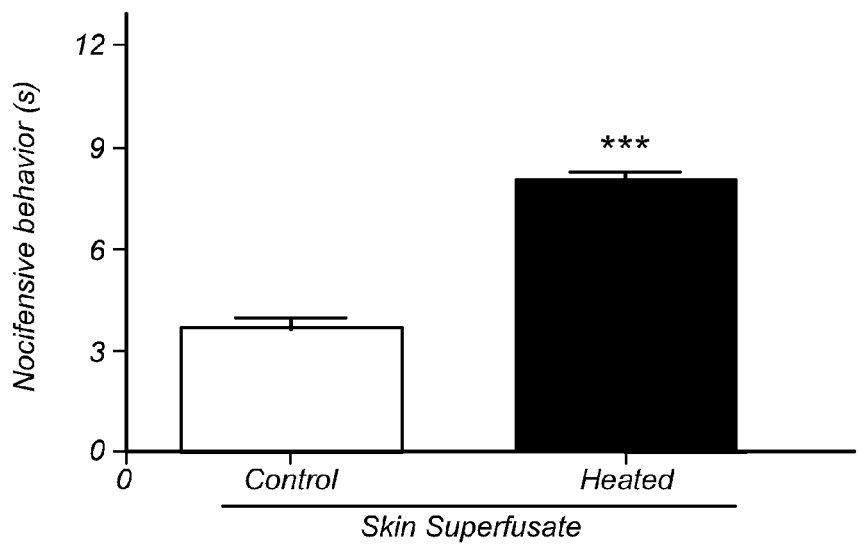
FIG. 2 depicts a bar graph showing the effects of heat on the release of oxidized linoleic acid metabolites in skin.

FIG. 2 depicts that heat evokes the release of oxidized linoleic acid metabolites from isolated and superfused skin biopsies. The enzyme immunoassay (EIA) analyses of compounds released into mouse skin superfusates demonstrated an increased presence of the linoleic acid oxidation products 9-HODE in the heated skin samples, compared with the non-heated samples (FIG. 2). The EIA finding is important for demonstrating the detection of μM quantities (~3 μg in 1 ml) of released 9-HODE when assayed immediately after collection.

Figure 3A:
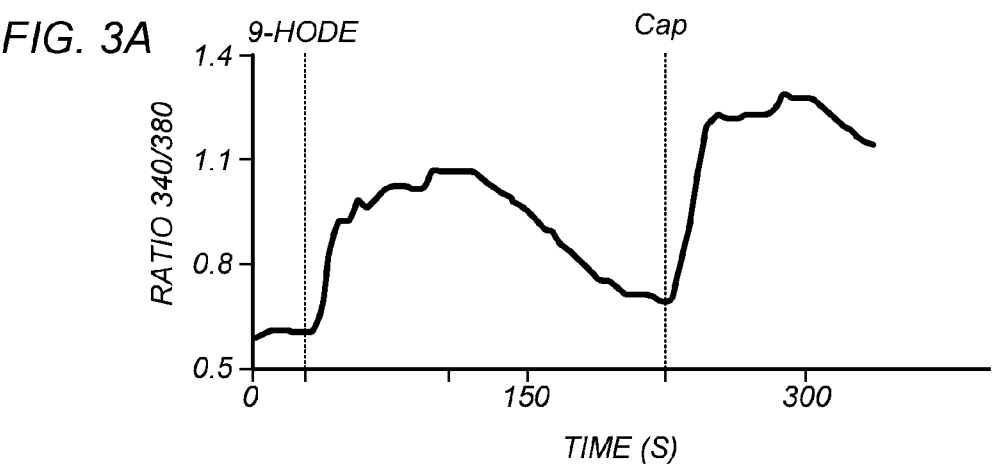
FIG. 3A depicts a graph demonstrating the increase in $[Ca^{2+}]i$ levels in TG neurons from WT mice evoked by 9-HODE.
Figure 3B:
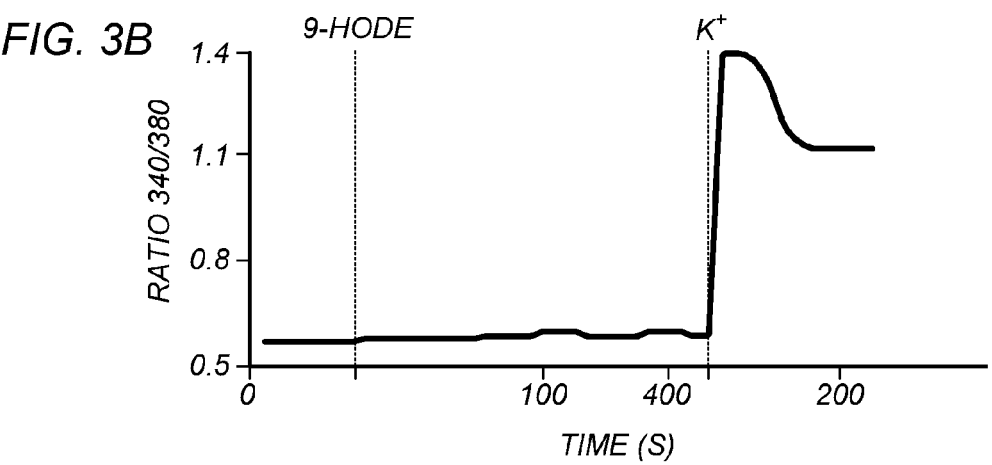
FIG. 3B depicts a graph demonstrating the $[Ca^{2+}]i$ levels in TG neurons from TRPV1 knockout (KO) mice after application of 9-HODE.
Figure 3C:
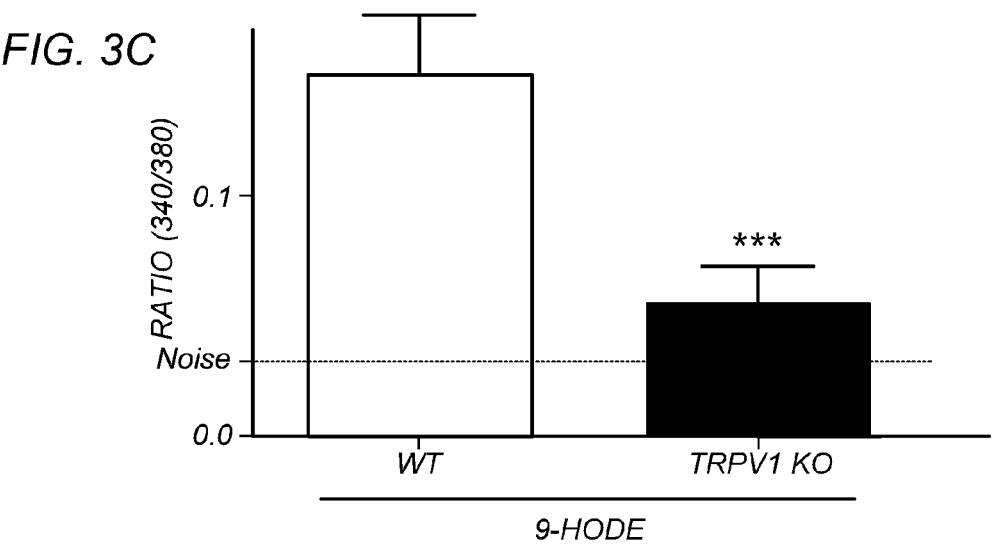
FIG. 3C depicts a bar graph comparing $[Ca^{2+}]i$ levels in TG neurons from WT versus TRPV1 KO mice after application of 9-HODE.
Figure 3D:
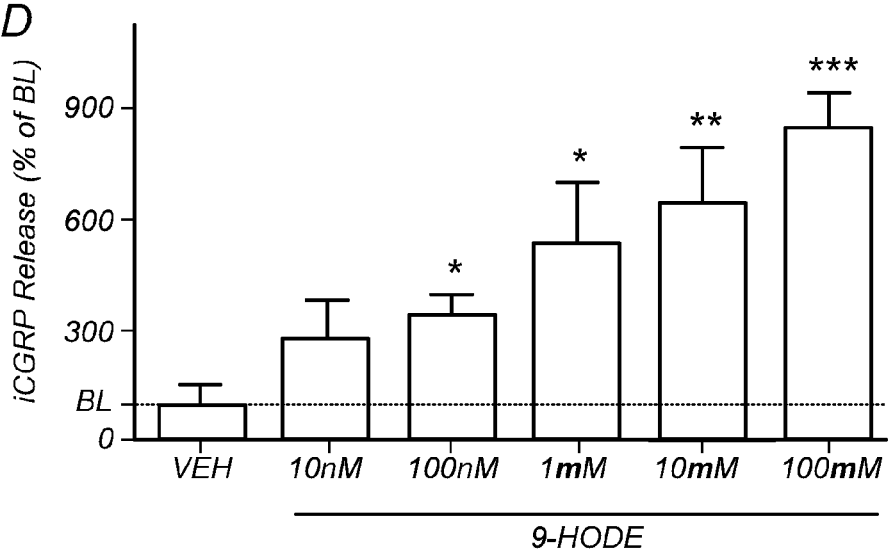
FIG. 3D depicts a concentration-effect curve demonstrating the stimulatory effect of 9-HODE on iCGRP release from cultured rat TG neurons.
Figure 3E:
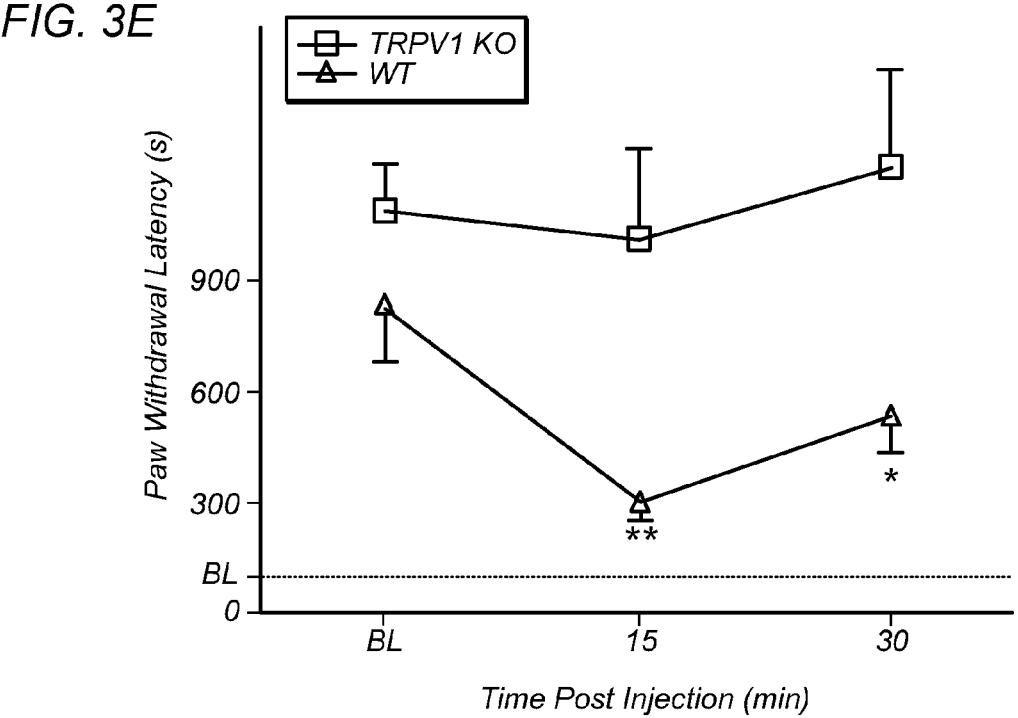
FIG. 3E depicts the effect of intraplantar (ipl) hindpaw injection of 9-HODE on pain behavior in wild type (WT) vs TRPV1 KO mice.
Figure 3F:
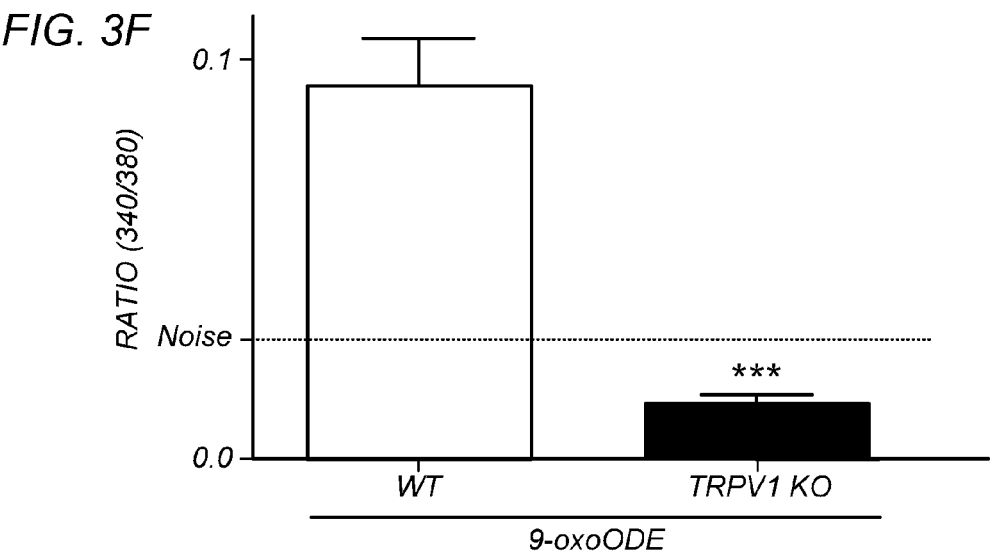
FIG. 3F depicts a comparison of increased $[Ca^{2+}]i$ levels in TG neurons from WT versus TRPV1 KO mice evoked by 9-oxoODE.
Figure 3G:
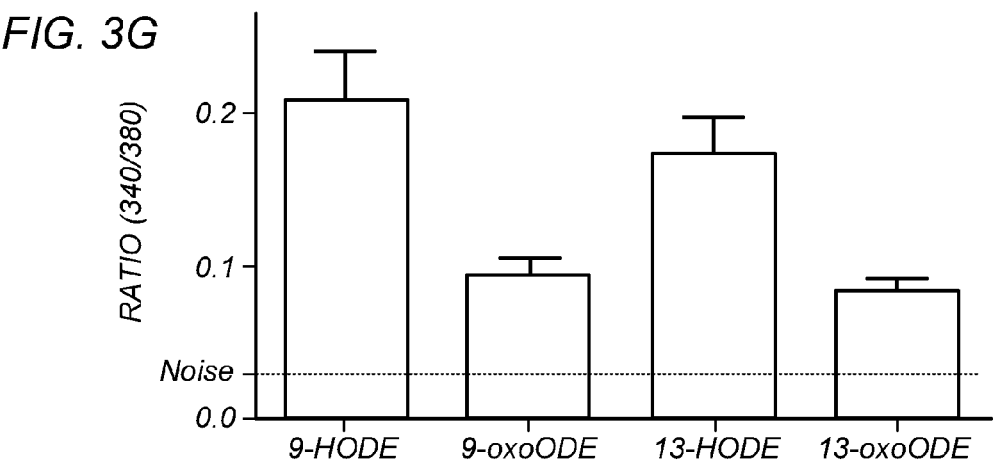
FIG. 3G depicts a comparison of increased $[Ca^{2+}]i$ levels in CHO cells expressing TRPV1 evoked by various linoleic acid metabolites.
Figure 3H:
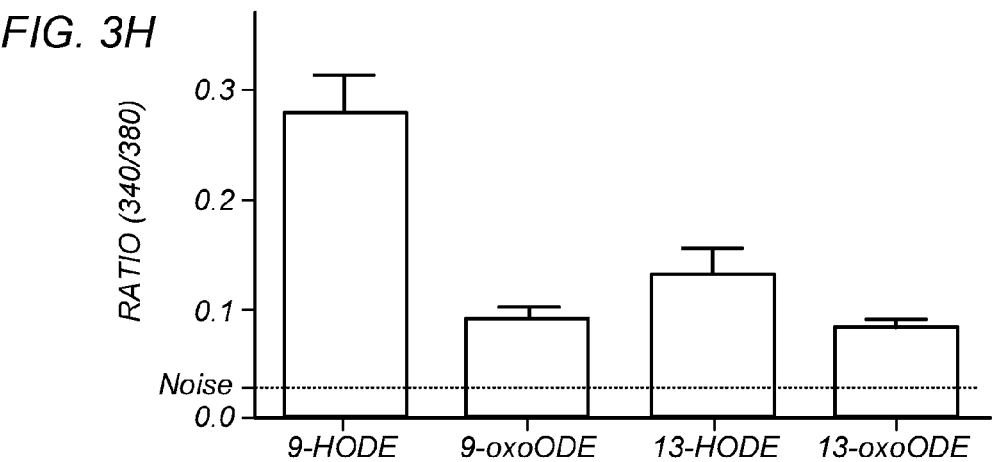
FIG. 3H depicts a summary of increased $[Ca^{2+}]i$ levels in cultured TG neurons from WT mouse evoked by various linoleic acid metabolites.

FIGS. 3A-H depict that lipoxy linoleic acid metabolites are TRPV1 agonists. The pharmacological activity of synthetic 9-HODE and related compounds on sensory neurons was characterized. Application of 9-HODE (100 μM) evoked a robust response in TG neurons cultured from WT mice (FIG. 3A), but not in neurons from TRPV1 KO mice (FIG. 3B, 50 mM potassium was positive control to verify neuronal viability). Detailed analysis of multiple experiments revealed that the neuronal population that responded to 9-HODE in WT mice coincided completely (75/75) with the capsaicin-sensitive subpopulation of neurons. The application of 9-HODE to neurons cultured from TRPV1 KO mice revealed a slight response in 4% of tested neurons (3/66); however, both the magnitude of $[Ca^{2+}]i$ accumulation and its time course were greatly reduced compared to WT neurons (FIG. 3C). The application of 9-HODE to cultured rat TG neurons produced a concentration-dependent increase in CGRP release, with effects evident at 10 nM and an $EC_{50}$~300 nM (FIG. 3D). Using observers blinded to treatment allocation, hindpaw intraplantar (ipl) injections of 9-HODE produced significantly greater thermal allodynia in WT mice but not in TRPV1 KO mice (FIG. 3E). Application of 9-oxoODE, a metabolite of 9-HODE, also triggered increased $[Ca^{2+}]i$ levels, but only in TG neurons from WT mice and not in neurons from TRPV1 KO mice (FIG. 3F). Another major metabolic pathway of linoleic acid leads to formation of 13-HODE and its metabolite, 13-oxoODE. The relative efficacy of these four compounds for evoked $[Ca^{2+}]i$ levels was evident when tested in cultured neurons from WT mice (FIG. 3G) and in TRPV1-expressing CHO cells (FIG. 3H).

Figure 4A:
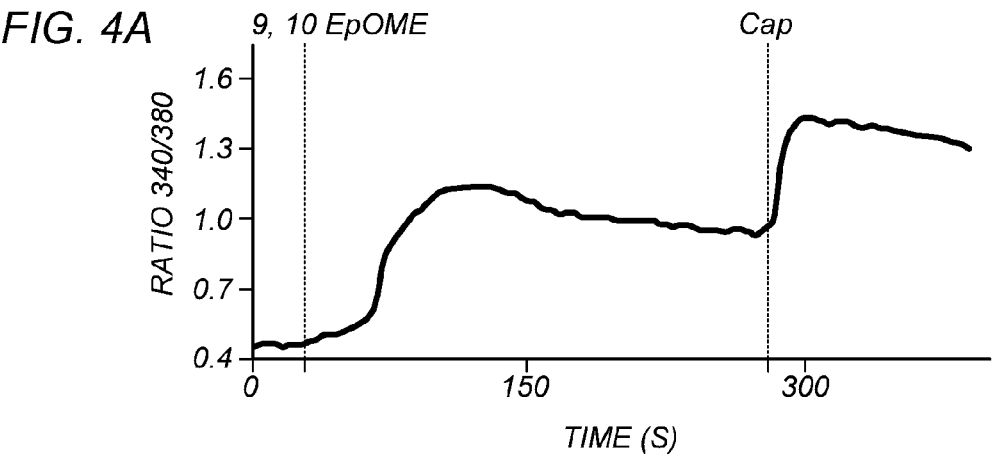
FIG. 4A depicts a graph showing $[Ca^{2+}]i$ levels in TG neurons from WT mice evoked by 9,10-EpOME.
Figure 4B:
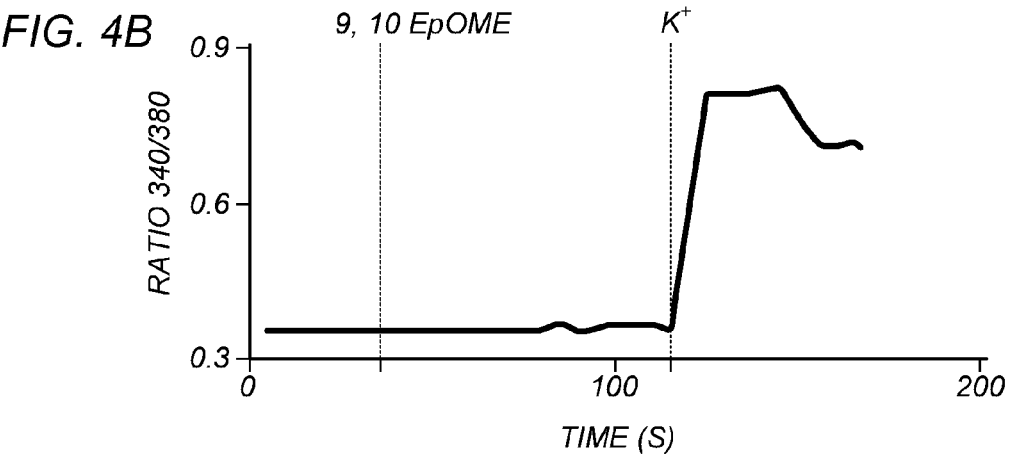
FIG. 4B depicts a graph showing $[Ca^{2+}]i$ levels in TG neurons from TRPV1 knockout (KO) mice after application of 9,10-EpOME.
Figure 4C:
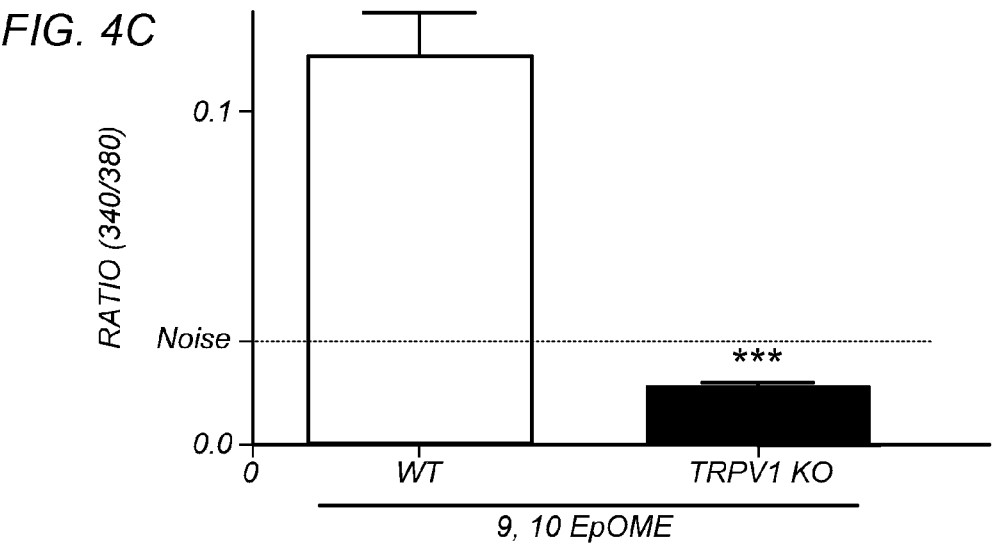
FIG. 4C depicts a bar graph showing $[Ca^{2+}]i$ levels in TG neurons from WT versus TRPV1 KO mice after application of 9,10-EpOME.
Figure 4D:
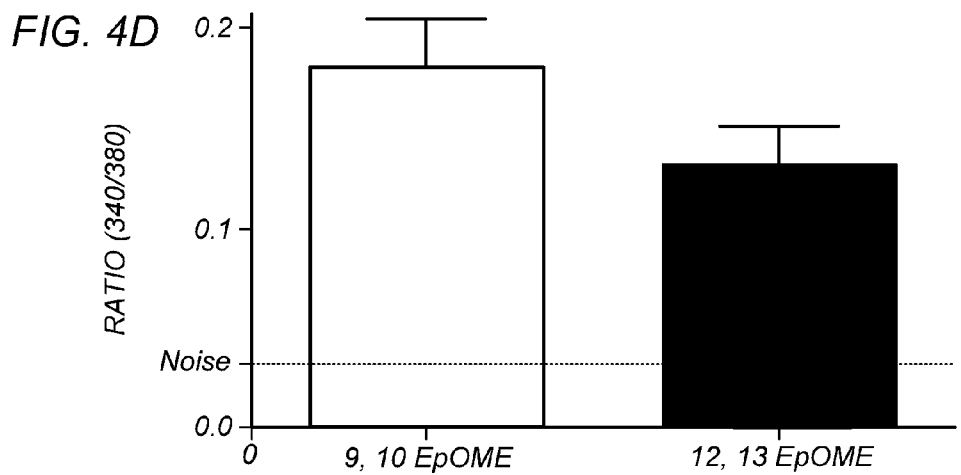
FIG. 4D depicts a comparison of $[Ca^{2+}]i$ levels in TG neurons after application of either 9,10 ERpOME or 12,13EpOME.
Figure 4E:
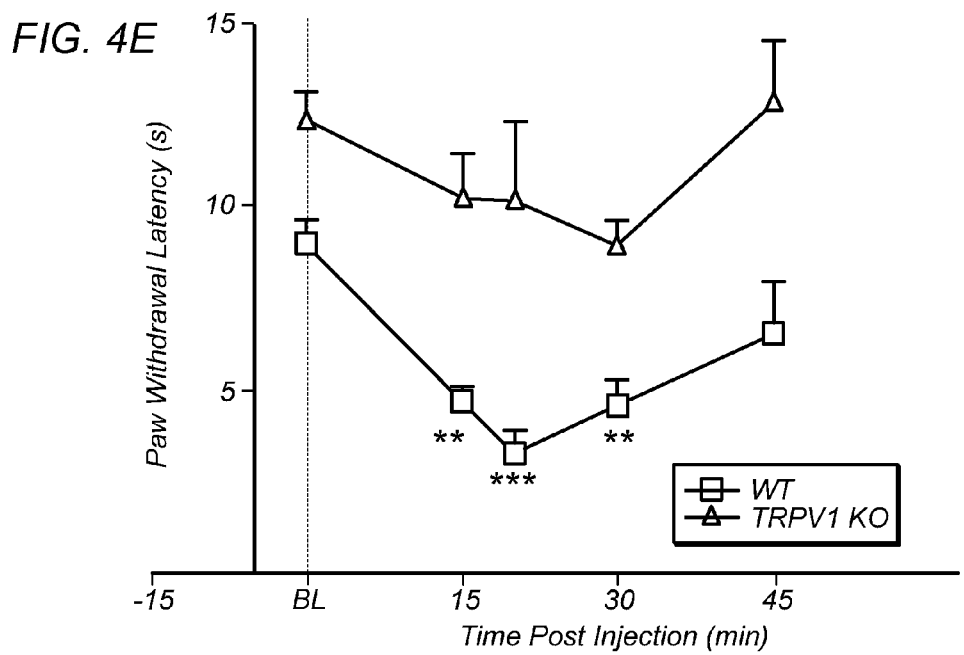
FIG. 4E depicts the effect of intraplantar (ipl) hindpaw injection of 9,10-EpOME on pain behavior in wild type (WT) vs TRPV1 KO mice.
Figure 4F:
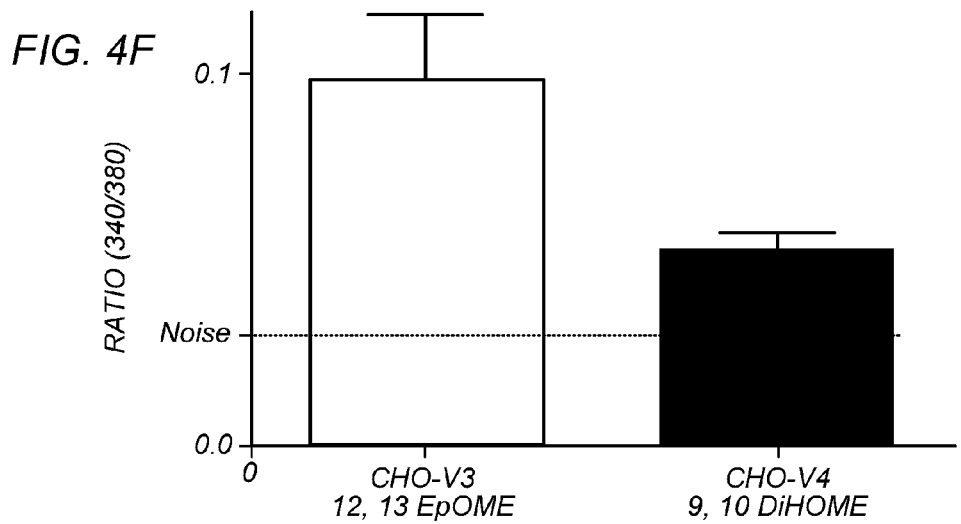
FIG. 4F depicts the effect of increased $[Ca^{2+}]i$ levels in CHO cells expressing either TRPV3 or TRPV4 after application of either 12,13 EpOME or 9,10EpOME.

FIGS. 4A-F depict that epoxy linoleic acid metabolites are also TRPV1 agonists. The epoxy metabolite, 9,10 EpOME (also known as leukotoxin), is highly elevated in burn patients and is implicated in shock in these patients. Similar to the previous studies on the HODEs, the application of 9,10 EpOME (100 μM) evoked calcium accumulation only in capsaicin-sensitive neurons (58/58) from WT mice (FIG. 4A), but not from TRPV1 KO mice (0/58) (FIG. 4B). A comparison of respective responses is demonstrated in FIG. 4C. A parallel epoxy metabolite, 12,13 EpOME, was also found to be a TRPV1 agonist and relative efficacy in CHO cells expressing TRPV1 is shown in FIG. 4D. 9,10 EpOME (50 μg/ipl) evoked thermal allodynia in WT mice that was absent in TRPV1 KO mice (FIG. 4E). These data demonstrate that TRPV1 activating activity of linoleic acid products extends to epoxy products as well. Upon screening of these metabolites against other heat-sensitive TRP channels, it was discovered that 12,13-EpOME is a TRPV3 agonist and 9,10-DiHOME is a TRPV4 agonist.

Figure 5A:
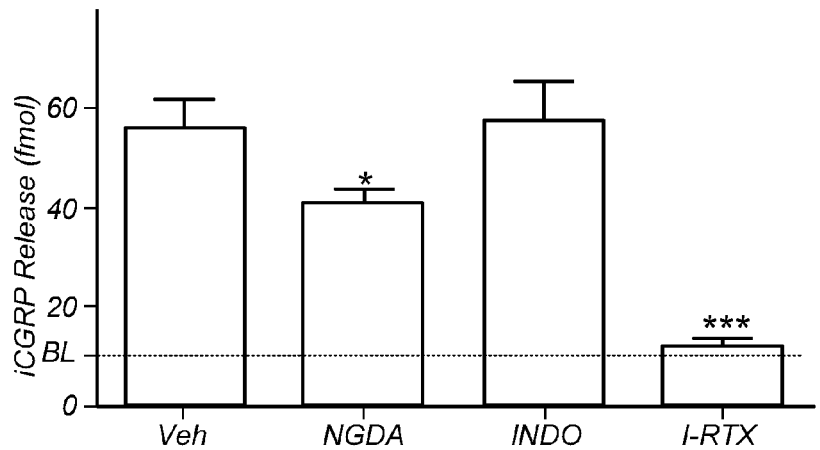
FIG. 5A depicts a comparison of the effect of NDGA (10 uM), Indomethacin (COX inhibitor, 2 uM) and I-RTX (a TRPV1 antagonist, 200 nM) on heat-evoked iCGRP release from rat TG neurons.
Figure 5B:
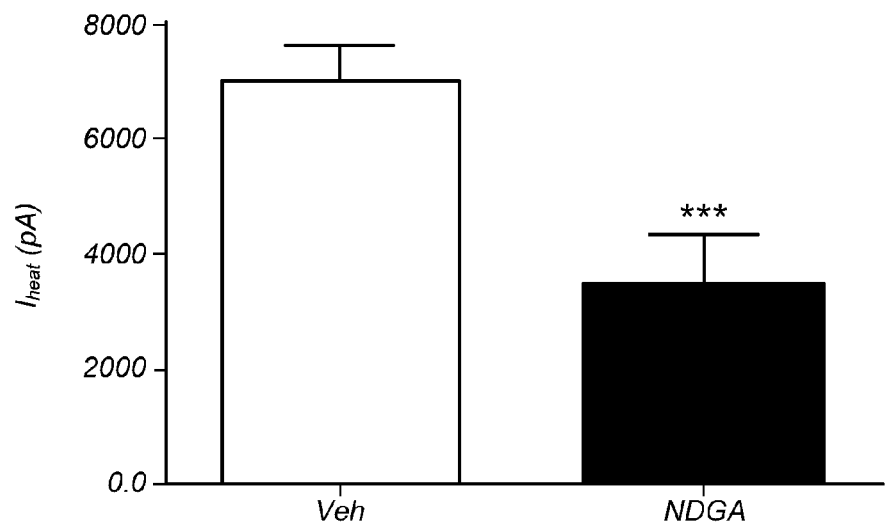
FIG. 5B depicts a bar graph summarizing the effect of NDGA (30 uM) on heat (48° C.)-evoked inward current in rat TG neurons.
Figure 5C:
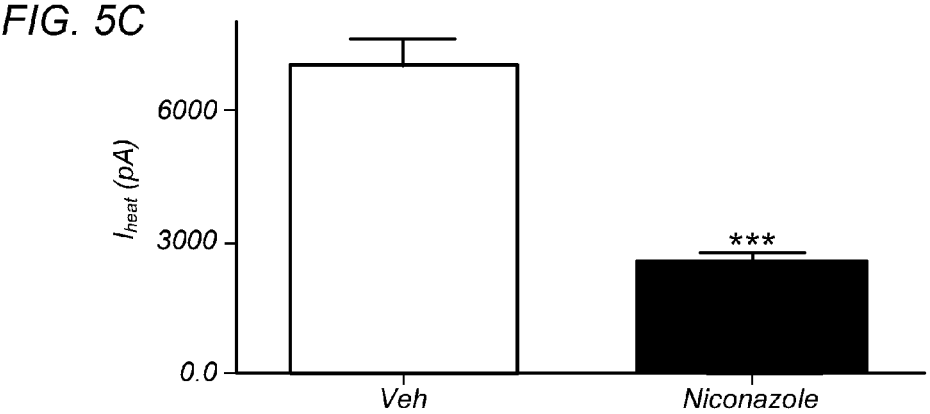
FIG. 5C depicts a bar graph summarizing the effect of miconazole (100 uM) on heat (48° C.)-evoked inward current in rat TG neurons.
Figure 5D:
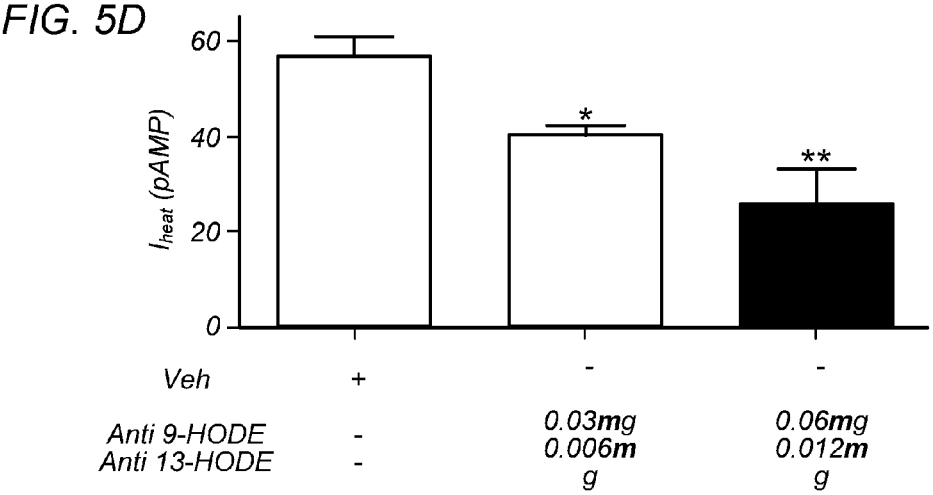
FIG. 5D depicts a bar graph demonstrating the effect of antibodies against 9 and 13-HODE applied intracellularly at two different concentrations on heat (48° C.)-evoked inward current in rat TG neurons.

FIGS. 5A-D depict that interventions reducing production or action of linoleic acid oxidation products results in decreased thermal pain. Whether heat-evoked activation of rat TG neurons is inhibited by interventions directed against linoleic acid metabolites was evaluated. Since oxidized linoleic acid metabolites can be formed either enzymatically (via lipoxygenase) or spontaneously (via free radicals), nor-dihydroguaiaretic acid (NDGA) was selected to block their synthesis since this compound inhibits both pathways. In a CGRP release assay, heat-evoked (48° C.) iCGRP release was partially reversed by pretreatment with NDGA and I-RTX but not by a COX-inhibitor indomethacin (FIG. 5A). Using patch clamp electrophysiology, the local application of a heat step (48° C.) produced a strong inward current ($I_{heat}$) in TG neurons. Pretreatment with NDGA produced ~50% reduction ($p<0.05$) in $I_{heat}$ (FIG. 5B). In a similar patch clamp electrophysiology set up, pretreatment with miconazole (100 uM) produced more than 75% reduction ($p<0.001$) in $I_{heat}$ (FIG. 5C). Whether intracellular immunoneutralization against 9-HODE and 13-HODE alters the responsiveness of sensory neurons to noxious heat was evaluated next. A solution containing both anti-9-HODE and anti-13-HODE antibodies (concentrations of 0.03-0.06 ug and 0.006-0.012 ug/patch pipette respectively) was delivered intracellularly via dialysis for 5 min prior to the application of a heat step (48° C.). This treatment combination significantly decreased $I_{heat}$ by up to 54% ($p<0.05$; FIG. 5D). Dialysis of each antibody alone did not significantly reduce $I_{heat}$, implicating a redundancy in the signaling properties of these compounds.

Figure 8A:
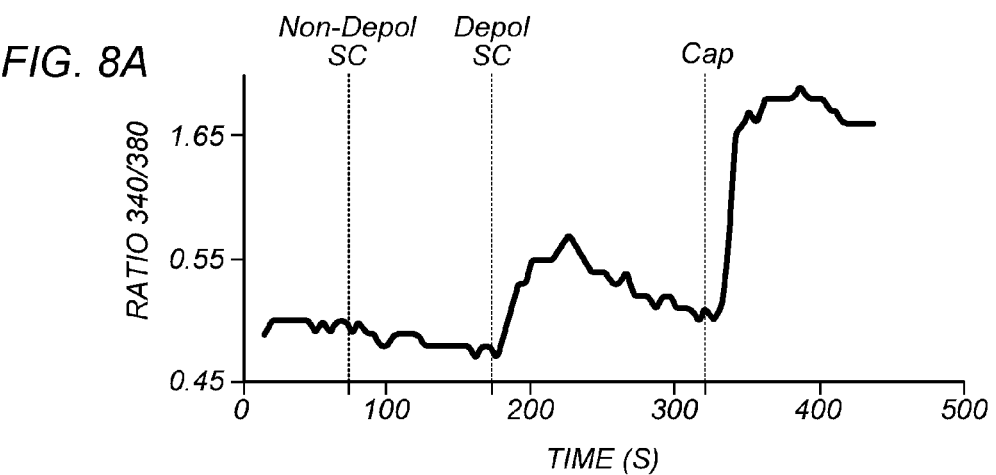
FIG. 8A depicts a graph of the release of endogenous TRPV1 agonists from depolarized spinal cords.
Figure 8B:
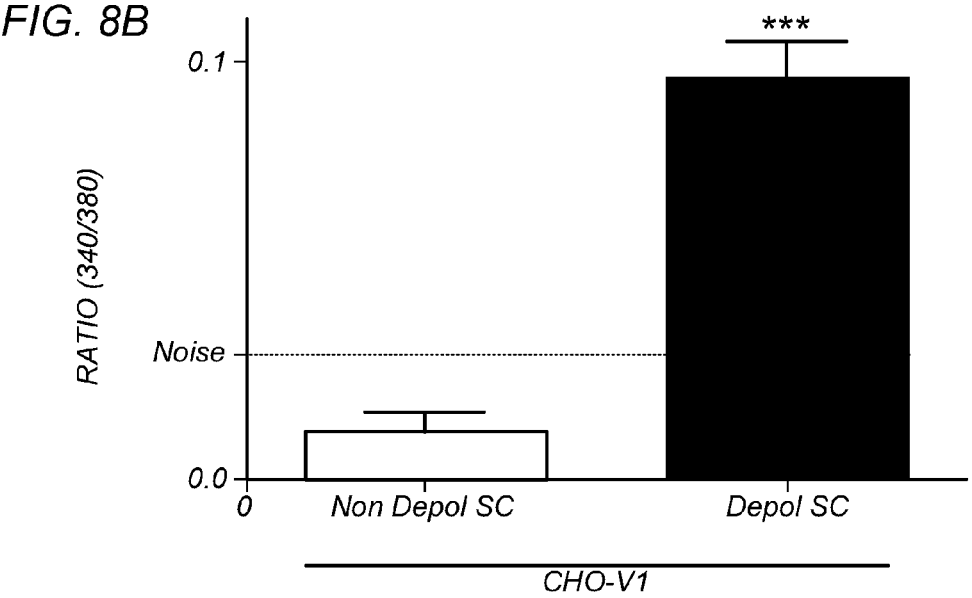
FIG. 8B depicts a comparison of change in $[Ca^{2+}]i$ evoked by superfusate from non-depolarized spinal cord and depolarized spinal cord in CHO cells expressing TRPV1.
Figure 8C:
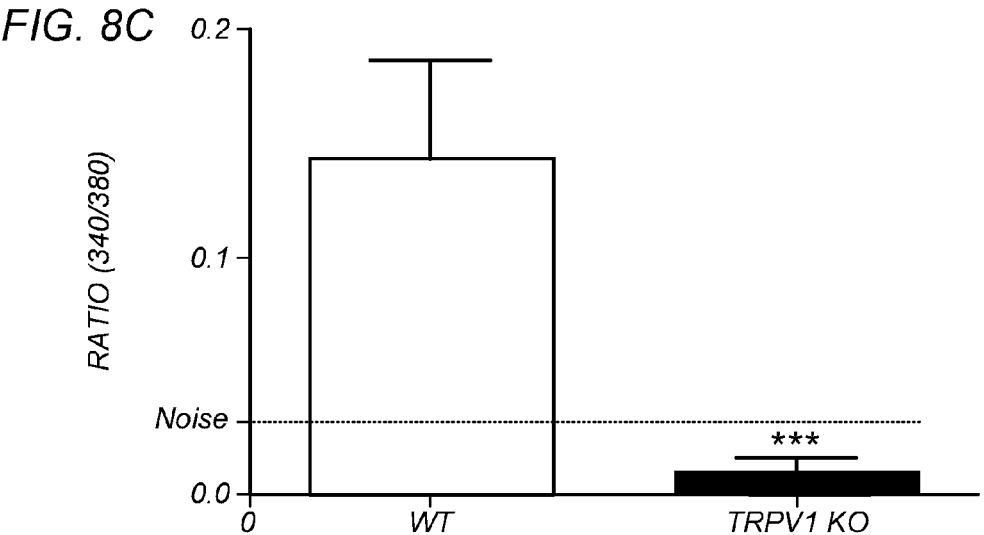
FIG. 8C depicts a comparison of a change in $[Ca^{2+}]i$ evoked by superfusate from depolarized spinal cord in TG neurons from WT mice and TRPV1 knockout mice.
Figure 8D:
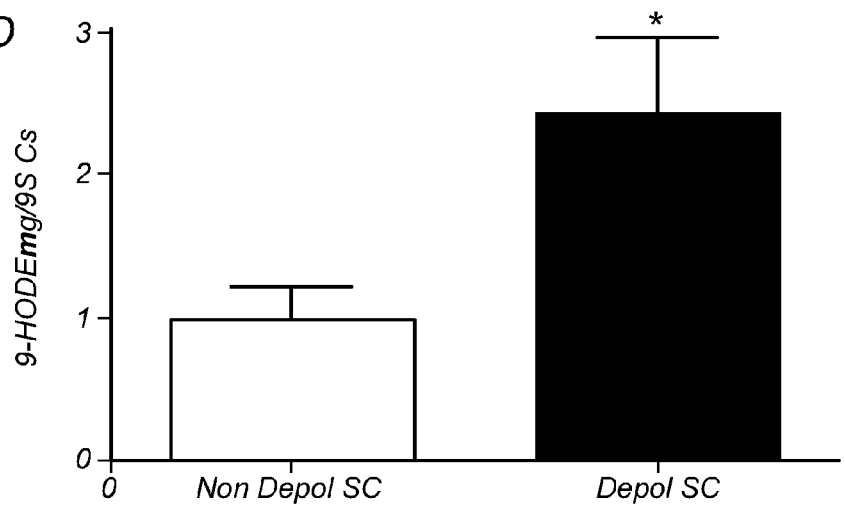
FIG. 8D depicts the change in the content of 9-HODE in the superfusate caused by exposure of spinal cords to depolarizing solution.

FIGS. 8A-D depict that depolarization of the spinal cord leads to release of endogenous TRPV1 ligand(s) that coincides with increased 9-HODE in the superfusate. TRPV1 in the spinal cord is critically involved in the maintenance of inflammatory hyperalgesia/allodynia. This suggests that TRPV1 in the spinal cord is tonically activated in inflammatory conditions. One possibility is that ongoing discharge in the primary afferent neurons leads to the release of an endogenous TRPV1 ligand in the spinal cord and this ligand in tern tonically activates TRPV1. To test this hypothesis, freshly isolated rat spinal cords (9) was depolarized using 50 mM potassium and the resulting superfusates were purified using $C_{18}$ columns similar to the previous skin experiments described herein above. Purified depolarized spinal cord superfusate activated CHO cells transfected with TRPV1, but purified superfusate obtained from the same spinal cords under basal (non-depolarized) conditions was unable to do so (FIGS. 8A-B). The specificity of the depolarized superfusate was further confirmed by its inability to activate any neurons from TRPV1 KO mice in contrast to a robust response in neurons from WT mice (FIG. 8C). EIA analysis demonstrated that depolarized spinal cord superfusate had a significantly higher 9-HODE content than the non-depolarized superfusate (FIG. 8D). Thus, the oxidized linoleic acid metabolites are released from both peripheral tissues and central neurons.

Figure 9A:
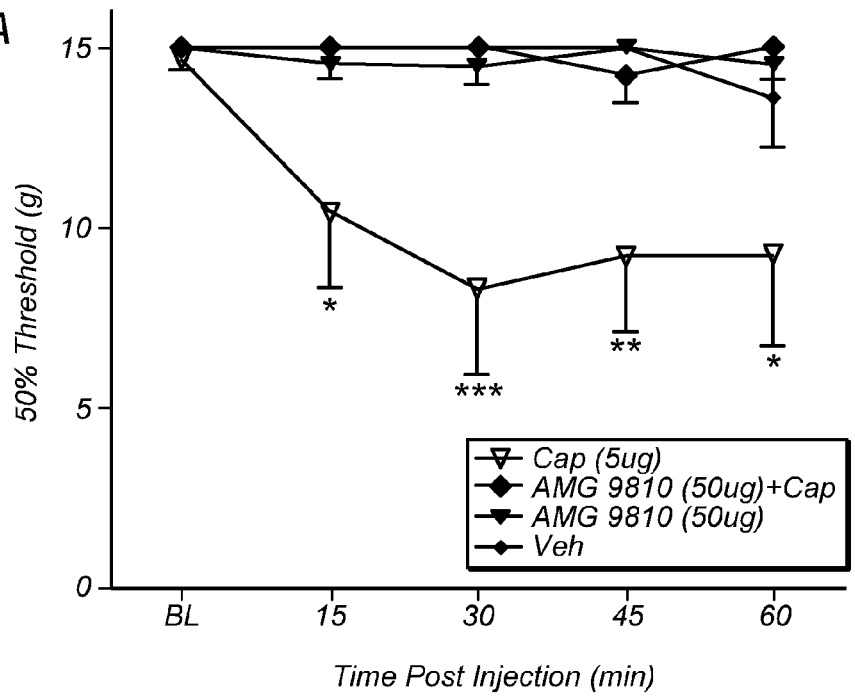
FIG. 9A depicts a comparison of the effect of intrathecal administration of Vehicle, a TRPV1 antagonist AMG 9810, and capsaicin with or without the TRPV1 antagonist on tactile allodynia observed in the right hindpaw of rats.
Figure 9B:
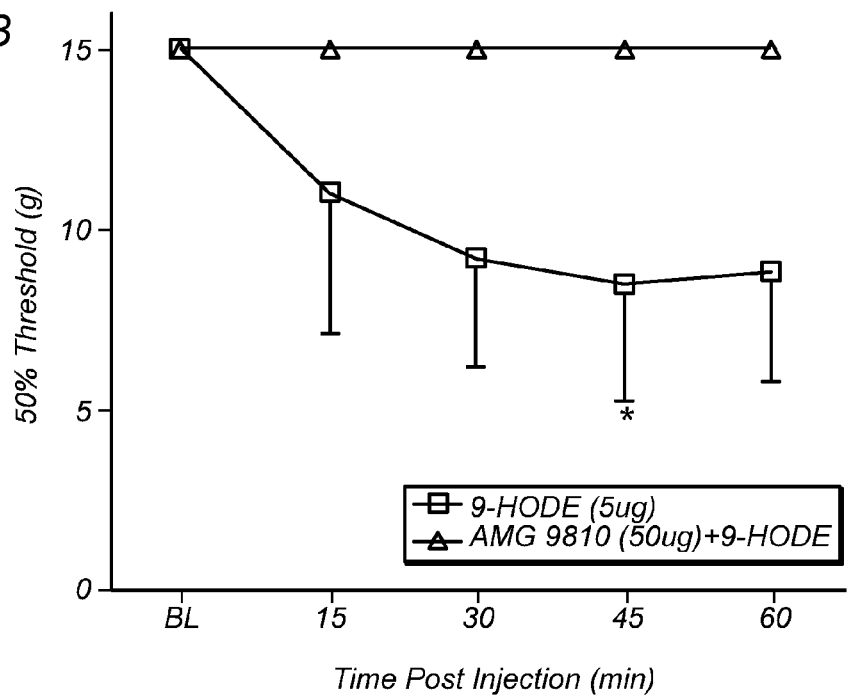
FIG. 9B depicts a comparison of the tactile allodynia evoked by intrathecal administration of 9-HODE in presence and absence of the TRPV1 antagonist AMG 9810 (50 ug)
Figure 9C:
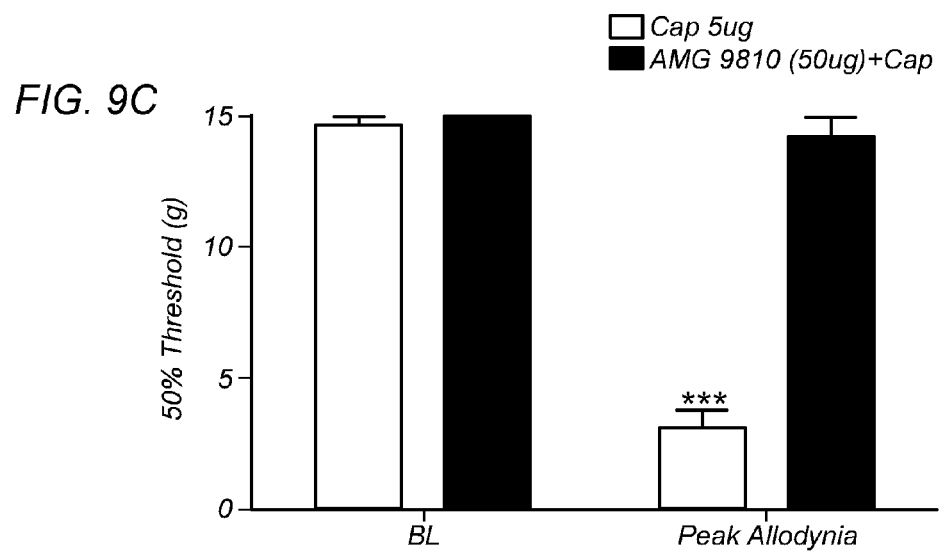
FIG. 9C depicts a comparison of the peak tactile allodynia evoked by capsaicin in presence and absence of AMG 9810.
Figure 9D:
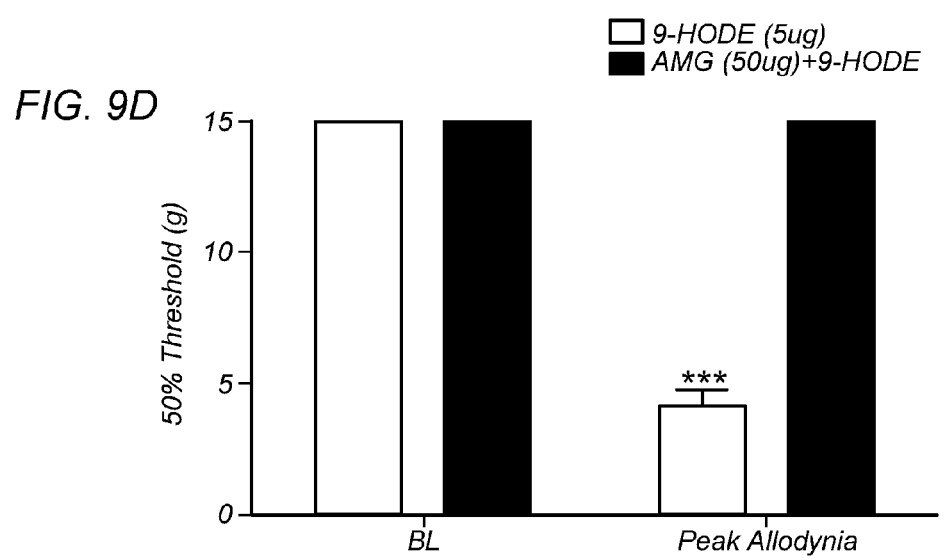
FIG. 9D depicts a comparison of the peak tactile allodynia evoked by 9-HODE in presence and absence of AMG 9810.

FIGS. 9A-D depict that spinal injection (intrathecal) of capsaicin or 9-HODE into the spinal cord space results in tactile allodynia. This effect is mediated by activation of TRPV1 since it is blocked by a TRPV1 antagonist (AMG 9810). Since it has been established that a depolarized spinal cord contains significantly greater amounts of 9-HODE, the ability of 9-HODE to evoke tactile allodynia upon intrathecal application was next evaluated. The results were compared with the results obtained with the positive control capsaicin. Indeed, in rats, intrathecal application of capsaicin (5 ug) evoked tactile allodynia that lasted 1 hour post injection and was completely reversible by a TRPV1 antagonist AMG 9810 (50 ug, FIG. 9A). Neither the vehicle nor AMG 9810 alone had any effect on mechanical withdrawal thresholds in rats. The intrathecal injection of synthetic 9-HODE at the same dose (5 ug) evoked tactile allodynia that was of similar magnitude and duration to that of capsaicin. Moreover, the effect of 9-HODE was also completely reversible by AMG 9810, suggesting exclusive involvement of TRPV1 in mediating the effect (FIG. 9B). Comparison of the peak effect evoked by both capsaicin and 9-HODE is shown in FIGS. 9C-D. The effects were remarkably similar.

Figure 10:
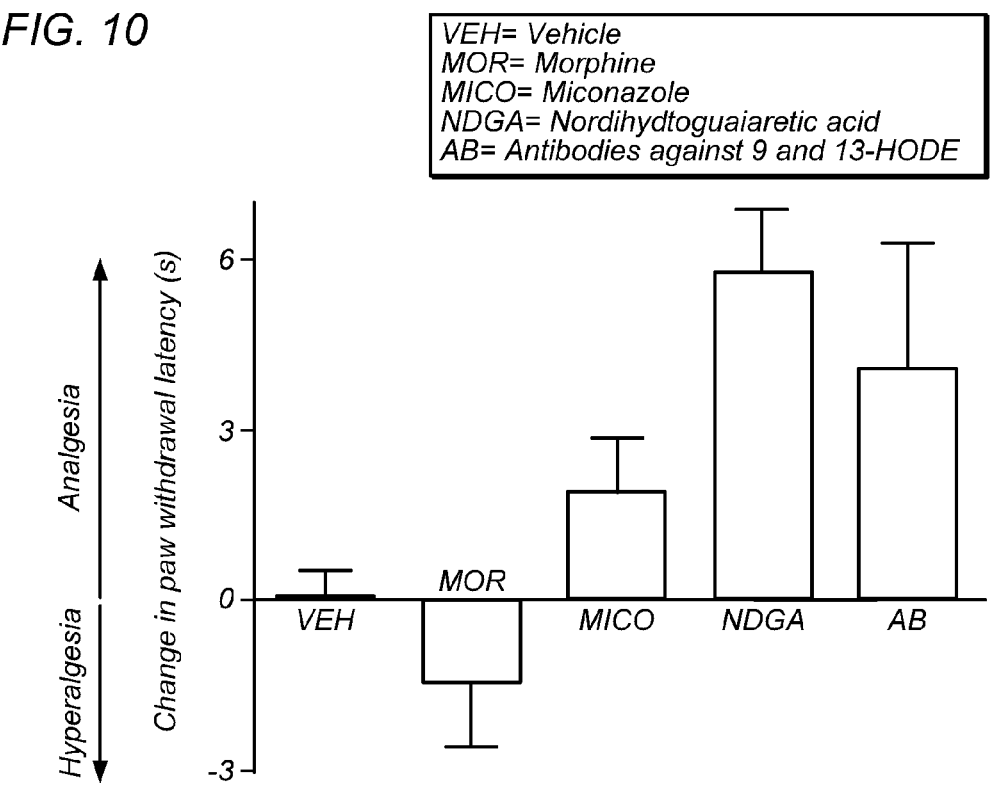
FIG. 10 depicts a comparison of antinociception for various treatments at a 15 minute time interval with demonstration of effects due to compounds that block the synthesis of linoleic acid metabolites (eg., NDGA) and compounds that block the actions of linoleic acid metabolites (Ab=antibodies)

FIG. 10 depicts the behavioral significance of blockade of linoleic acid oxidation on thermal nociception in rats. The intraplantar hindpaw (ipl) injection of NDGA, miconazole, and a combination of anti 9-HODE and anti-13-HODE was compared to morphine sulfate, a gold standard analgesic. The examined doses only produced a locally mediated effect, since the responses were only observed in the ipsilateral (injected) hindpaw and not in the contralateral paw. Under these conditions, miconazole, NDGA and the antibodies all produced a thermal antinociception far beyond that of the vehicle or morphine injected rats. The studies were performed in a separate groups of animals for each condition and by observers blinded to treatment allocation (all compounds at 100 ug/paw and antibodies were each 25 ug/paw) (FIG. 10). Thus, compounds that inhibit the synthesis or actions of linoleic acid metabolites produce significant pain relieving effects in mammals. Moreover, at comparable dosages, these linoleic acid inhibitors produce far greater analgesia than morphine sulfate.

Figure 11:
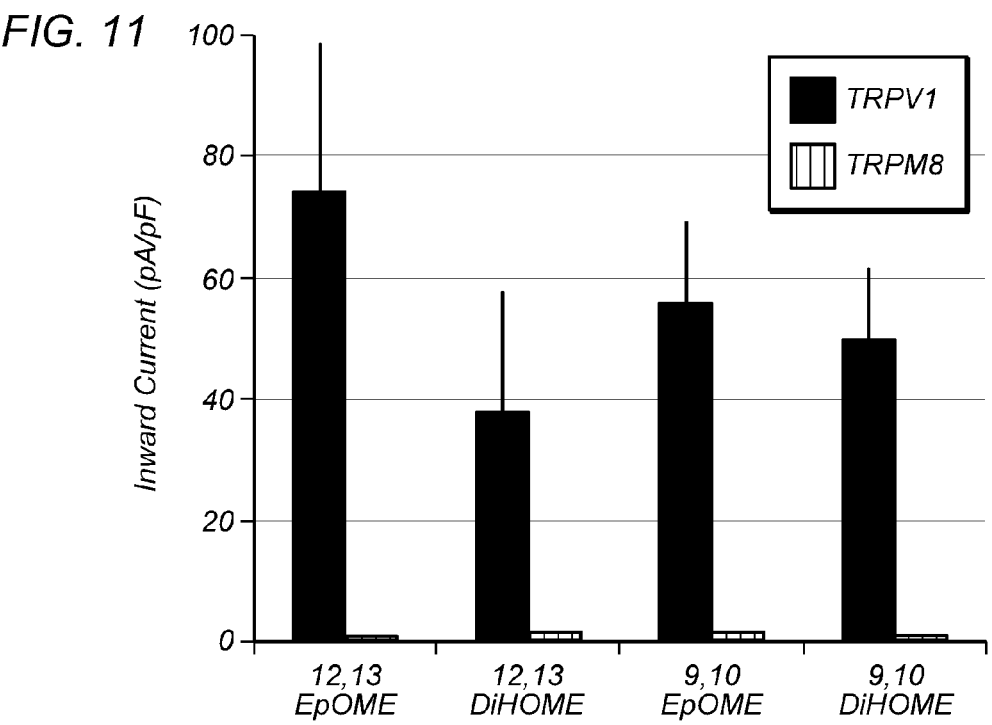
FIG. 11 depicts the effect of various oxidized linoleic acid metabolites on the activity of TRPA1 or TRPM8 ion channels.

FIG. 11 depicts the effect of various oxidized linoleic acid metabolites on the activity of TRPA1 or TRPM8 ion channels. The oxidized linoleic acid metabolites were found to be agonists for the TRPA1 ion channel This ion channel is important for detection of pain and other pathological states and therefore drugs that block the synthesis or actions of the oxidized linoleic acid metabolites may be useful for treatment of pain, shock and inflammation via reduction of TRPA1 activities. Whole cell patch clamp electrophysiological recordings of CHO (Chinese Hamster Ovary) cells transfected with either TRPA1 or TRPM8 show a striking response. The oxidized linoleic acid metabolites only activated the TRPA1 channel. There was no effect on the TRPM8 channel. Several important conclusions can be made. First, the oxidized linoleic acid metabolites demonstrate selectivity, since some, but not all TRP channels are activated. This is important in demonstrating a specific effect and in establishing the non-obvious nature of the overall findings. Second, the TRPA1 channel is strongly implicated in pain, whereas the TRPM8 channel is not. This indicates that drugs that block oxidized linoleic acid metabolite synthesis or activity will have a selective effect on pain, shock or inflammation rather than non-selectively altering all TRP channels.

Figure 12:
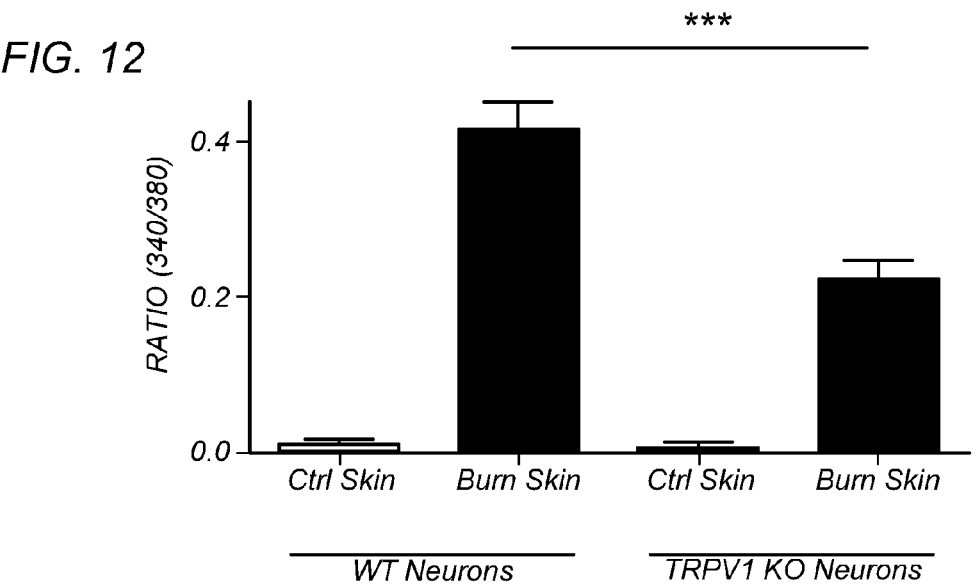
FIG. 12 depicts the effect of lipids extracted from burned human skin samples and applied to cultured trigeminal sensory neurons from control (wild type, "WT") mice and from TRPV1 knock-out mice.

FIG. 12 depicts the effect of lipids extracted from burned human skin samples against cultured trigeminal sensory neurons from control (wild type, "WT") mice and from TRPV1 knock-out mice. Samples of burned human skin and control (non-burned) human skin from patients undergoing treatment in a hospital burn ward were obtained. The lipids from the skin samples were extracted by incubation with acetonitrile and the samples dried under nitrogen gas. The samples were tested against cultured trigeminal sensory neurons from control (wild type, "WT") mice and from TRPV1 knock-out mice using real time imaging of calcium accumulation (fura-2 method). Extracts from human control (non burned) skin had no effect on activating neurons from either control (WT) or TRPV1 knockout (TRPV1 KO) mice. However, the extracts from burned human skin produced significant activation of neurons from WT mice. This effect was reduced significantly reduced in the TRPV1 KO neurons, although about 50% of the activity was remaining. Thus, similar to the oxidized linoleic acid metabolites, the extracts from burned human skin activate TRPV1 and some other channels.

Figure 13:
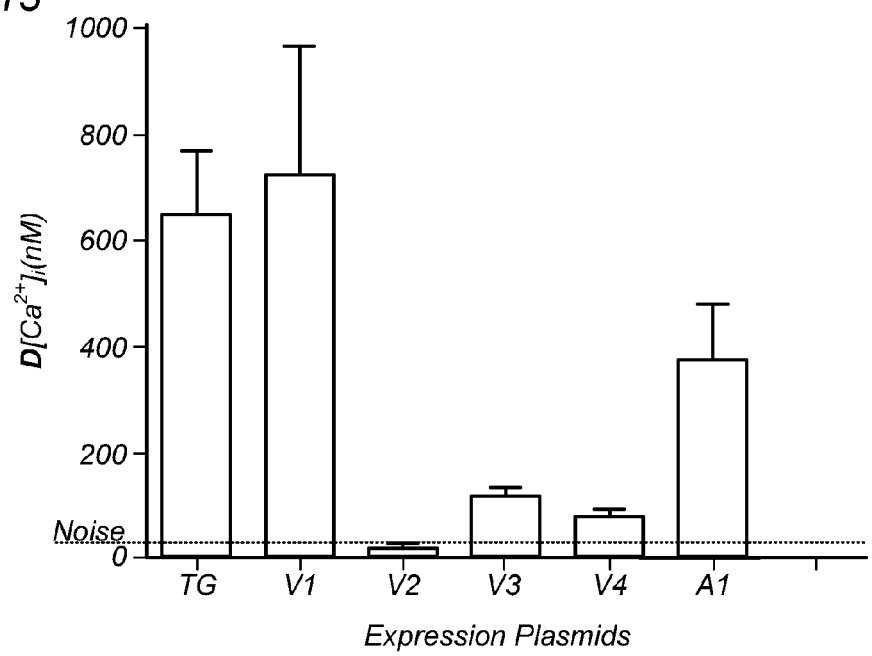
FIG. 13 depicts the effect of lipids extracted from burned human skin samples in CHO cells that expressed either TRPV1, TRPV2, TRPV3, TRPV4 or TRPA 1.

FIG. 13 depicts the effect of lipids, extracted from burned human skin samples, and then applied to CHO cells that expressed either TRPV1, TRPV2, TRPV3, TRPV4 or TRPA1, using real time calcium imaging. As shown, the extracts of the burned human skin activated TRPV1, TRPV3, TRPV4 and TRPA1, but not TRPV2. This shows that drugs that block the synthesis or actions of the oxidized linoleic acid metabolites would have strong effects for treating pain, shock or inflammation in patients suffering from pain conditions.

Collectively, these new data demonstrate the selectivity of the oxidized linoleic acid metabolites for activating TRP channels associated with pain, shock and inflammation, such as TRPV1, TRPV3, TRPV4 and TRPA1. In addition, the new data demonstrate that extracts from burned human skin in living patients activate sensory neurons via TRPV1 and activate CHO cells transfected with TRPV1, TRPV3, TRPV4 and TRPA1, suggesting that oxidized linoleic acid metabolites active TRP channels associated with pain, shock and inflammation in humans. Thus, drugs that block the synthesis or actions of these oxidized linoleic acid metabolites will have utility for treatment of pain, shock and inflammation.

Figure 14:
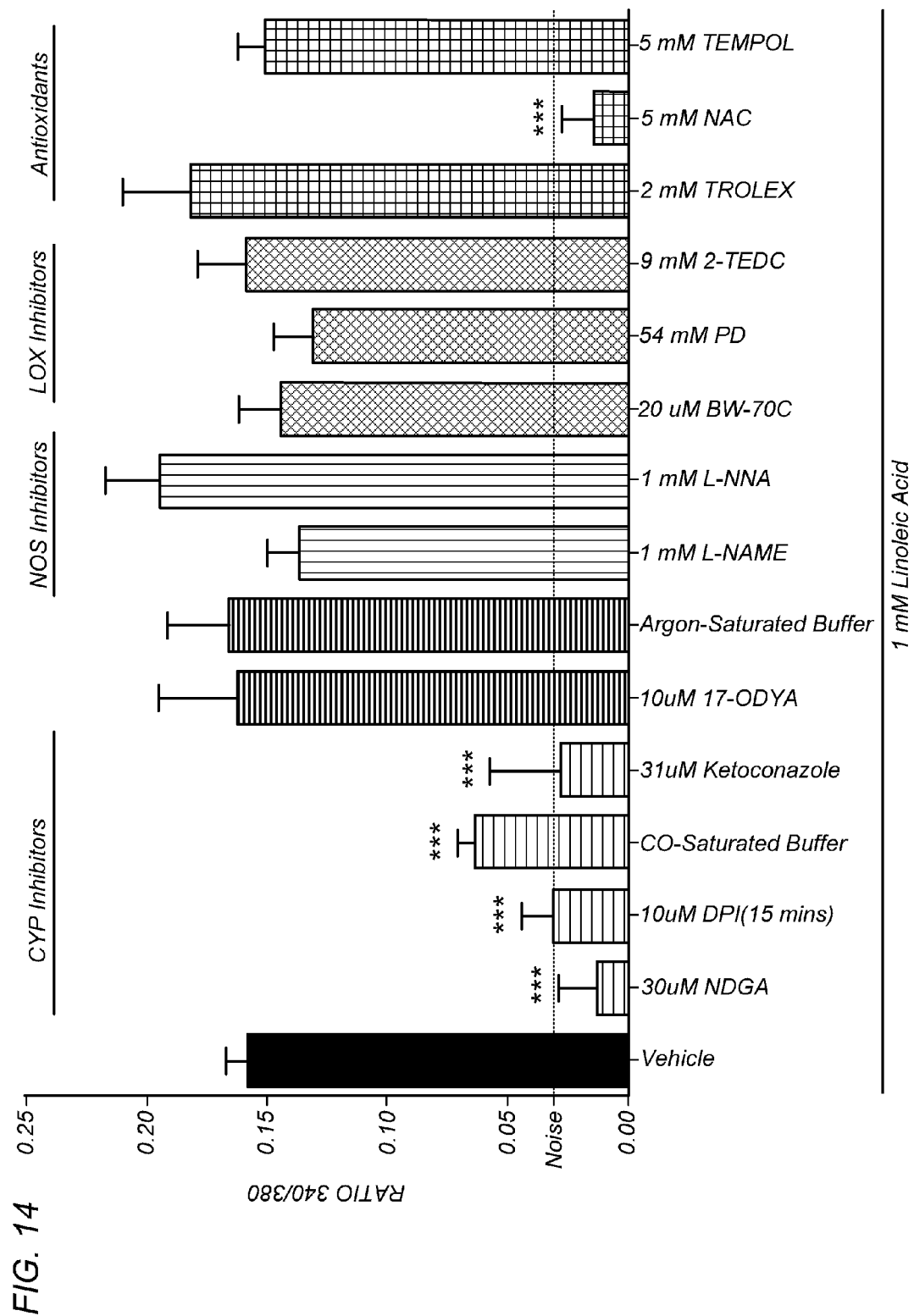
FIG. 14 depicts the effect of linoleic acid to activate rat trigeminal sensory neurons from mice in the presence of cytochrome P450 inhibitors, nitric oxide synthase inhibitors, lipoxygenase inhibitors and antioxidants.

FIG. 14 depicts the effects of pretreatment with either cytochrome P450 inhibitors (NDGA, DPI, CO or ketoconazole, ODYA), nitric oxide synthase inhibitors (L-NAME, L-NNA), lipoxygenase inhibitors (BW-70C, PD, TEDC) or antioxidants (TROLOX, NAC, TEMPOL) versus negative controls (vehicle, argon) on the ability of linoleic acid to activate rat trigeminal sensory neurons as measured by real time levels of intracellular calcium (Fura-2, as indicated by the ratio of 340/380). The following abbreviations are used:

1) NDGA: Nordihydroguaiaretic Acid
2) DPI: Diphenyliodonium
3) CO: Carbon Monoxide
4) 17-ODYA: 17-Octadecynoic acid
5) L-NAME: L-$N^G$-Nitroarginine methyl ester (hydrochloride)
6) L-NNA: $N^G$-nitro-L-Arginine; L-$N^G$-Nitroarginine
7) BW-70C: N-[3-[3-(Fluorophenoxy)phenyl]-1-methyl-2-propenyl]-N-hydroxyurea
8) PD146176: 6,11-Dihydro[1]benzothiopyrano[4,3-b]indole
9) 2-TEDC: 2-(1-Thienyl)ethyl 3,4-dihydroxybenzylidenecyanoacetate
10) TROLOX: 6-hydroxy-2,5,7,8-tetramethylchroman-2-carboxylic acid
11) NAC: N-Acetyl-L-cysteine
12) TEMPOL: 1-Oxyl-2,2,6,6-tetramethyl-4-hydroxypiperidine The results indicate that the P450 inhibitors, including ketoconozole, and certain antioxidants, completely blocked the ability of linoleic acid to activate pain neurons. Although DPI and CO block all cytochrome P450s, the linoleic acid metabolism is a specific effect since more selective P450 inhibitors (eg., ketoconazole vs ODYA) do not universally inhibit the formation of these neuron-activating compounds. Thus, ketoconazole inhibits the formation of linoleic acid metabolites and is analgesic, yet ODYA does not.

In this patent, certain U.S. patents, U.S. patent applications, and other materials (e.g., articles) may have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of treating burns in a subject comprising topically administering to a subject who would benefit from such treatment a therapeutically effective amount of a pharmaceutical composition, wherein the pharmaceutical composition comprises ketoconazole and nordihydroguaiaretic acid.

2. The method of claim 1, wherein the pharmaceutical composition comprises up to about 10% by weight of ketoconazole.

* * * * *